(12) United States Patent
Ma

(10) Patent No.: US 10,195,272 B2
(45) Date of Patent: Feb. 5, 2019

(54) ADOPTIVE T-CELL THERAPY USING FCεRI-BASED CHIMERIC ANTIGEN RECEPTORS FOR TREATING IGE-MEDIATED ALLERGIC DISEASES

(71) Applicant: THE NEMOURS FOUNDATION, Jacksonville, FL (US)

(72) Inventor: Zhengyu Ma, Garnet Valley, PA (US)

(73) Assignee: The Nemours Foundation, Jacksonville, FL (US)

( * ) Notice: Subject to any disclaimer, the term of this patent is extended or adjusted under 35 U.S.C. 154(b) by 22 days.

(21) Appl. No.: 15/084,192

(22) Filed: Mar. 29, 2016

(65) Prior Publication Data

US 2018/0193452 A1  Jul. 12, 2018

Related U.S. Application Data

(63) Continuation-in-part of application No. 15/058,286, filed on Mar. 2, 2016.

(60) Provisional application No. 62/127,024, filed on Mar. 2, 2015.

(51) Int. Cl.

| C07K 14/705 | (2006.01) |
|---|---|
| C07K 14/725 | (2006.01) |
| C12N 5/0783 | (2010.01) |
| C07K 16/28 | (2006.01) |
| A61K 39/395 | (2006.01) |

(52) U.S. Cl.
CPC ...... *A61K 39/3955* (2013.01); *C07K 14/7051* (2013.01); *C07K 14/7056* (2013.01); *C07K 16/2809* (2013.01); *C07K 16/2818* (2013.01); *C07K 16/2878* (2013.01); *C12N 5/0636* (2013.01); *C07K 2317/14* (2013.01); *C07K 2317/52* (2013.01); *C07K 2319/02* (2013.01); *C07K 2319/03* (2013.01); *C07K 2319/75* (2013.01)

(58) Field of Classification Search
None
See application file for complete search history.

(56) References Cited

U.S. PATENT DOCUMENTS

| 5,359,046 A * | 10/1994 | Capon ............... C07K 14/7051 435/235.1 |
|---|---|---|
| 2001/0033842 A1 * | 10/2001 | Jardieu ................ C07K 16/00 424/155.1 |
| 2003/0105000 A1 * | 6/2003 | Pero ....................... A61K 38/06 514/19.3 |
| 2005/0113564 A1 * | 5/2005 | Campana .......... C07K 14/70517 530/350 |
| 2013/0287748 A1 | 10/2013 | June et al. |
| 2015/0368342 A1 | 12/2015 | Wu et al. |

OTHER PUBLICATIONS

Kershaw (J. Biol. Chem. Aug. 30, 1996, 21214-21220) (Year: 1996).*
Kershaw et al (J. Leukocyte Biology Dec. 1996 60:721-728) (Year: 1996).*
Hakimi et al. (J. Biol. Chem. Dec. 25, 1990) (Year: 1990).*
Palladino et al. (Cancer Res. Feb. 1983 43:572-576) (Year: 1983).*
NP_932170.1 (T-cell surface glycoprotein CD3 zeta chain isoform 1 Nov. 3, 2013) (Year: 2013).*
Rudikoff et al. (PNAS USA, 1982, 79: 1979-1983) (Year: 1982).*
Coleman et al. (Research in Immunology, 1994; 145(1): 33-36) (Year: 1994).*
Burgess et al. (J of Cell Bio. 111:2129-2138, 1990) (Year: 1990).*
Ibragimova and Wade (Biophysical Journal, Oct. 1999, vol. 77, pp. 2191-2198) (Year: 1999).*
Jena et al. (Blood Aug. 19, 2010, 116 (7): 1035-1044) (Year: 2010).*
Almagro & Fransson, (Frontiers in Bioscience 2008; 13:1619-33) (Year: 2008).*
Brentjens et al., (2013) "CD19-targeted T cells rapidly induce molecular remissions in adults with chemotherapy-refractory acute lymphoblastic leukemia", Sci Transl Med 5:177ra138, pp. 1-19.
Scholler et al., (2012) "Decade-long safety and function of retroviral-modified chimeric antigen receptor T cells", Sci Transl Med 4:132ra153, pp. 1-16.
Kalos et al., (2011) "T cells with chimeric antigen receptors have potent antitumor effects and can establish memory in patients with advanced leukemia", Sci Transl Med. 2011;3(95):95ra73, pp. 1-21.
Zhong et al., "Chimeric antigen receptors combining 4-1BB and CD28 signaling domains augment PI3kinase/AKT/Bcl-XL activation and CD8+ T cell-mediated tumor eradication", Molecular Therapy (2010) 18 2, pp. 413-420.
Krogsgaard et al., "Evidence that structural rearrangemnts and/or flexibility during TCR binding can contribute to T cell activation", Mol Cell. 2003;12(6), pp. 1367-1378.
Turatti et al. (2007) "Redirected activity of human antitumor chimeric immune receptors is governed by antigen and receptor expression levels and affinity of interaction", J Immunother 30, pp. 684-693.
Hulett et al., (1999) "Fine structure analysis of interaction of FcepsilonRI with IgE", J Biol Chem 274, pp. 13345-13352.
Garman et al., (2000) "Structure of the Fc fragment of human IgE bound to its high-affinity receptor Fc epsilonRI alpha", Nature 406(6793), pp. 259-266.

(Continued)

*Primary Examiner* — Peter J Reddig
(74) *Attorney, Agent, or Firm* — Drinker Biddle & Reath LLP

(57) ABSTRACT

A chimeric antigen receptor (CAR) contains a human FcεRIα extracellular domain or a mutant FcεRIα extracellular domain that has a reduced binding affinity for human IgE compared to wild type human FcεRIα extracellular domain. The CAR further contains an intracellular signaling domain comprising at least one immunoreceptor-based activation motif (ITAM). The CAR may further comprise a costimulatory signaling domain, such as an intracellular domain of at least one of the costimulatory molecules 4-1BB, CD27, CD28, CD134 or ICOS. T cells transduced with vectors encoding the CAR are used in CAR-based adoptive T-cell therapy for targeting IgE-expressing B cells and treating IgE-mediated allergic diseases.

81 Claims, 7 Drawing Sheets

Specification includes a Sequence Listing.

(56) References Cited

OTHER PUBLICATIONS

Cook et al., (1997) "Identification of contact residues in the IgE binding site of human FcepsilonRIalpha", Biochemistry 36, pp. 15579-15588.
Blank et al., (1989), "Complete structure and expression in transfected cells of high affinity IgE receptor", Nature 337, pp. 187-189.
MacGlashan et al., (1997) "Down-regulation of Fc(epsilon)RI expression on human basophils during in vivo treatment of atopic patients with anti-IgE antibody", J Immunol 158, pp. 1438-1445.
Scheinfeld, (2005), "Omalizumab: a recombinant humanized monoclonal IgE-blocking antibody", Dermatol Online J 11 (1), pp. 1-3.
Shirasu et al., (2012) "Functional design of chimeric T-cell antigen receptors for adoptive immunotherapy of cancer: architecture and outcomes", Anticancer Res 32, pp. 2377-2383.
Finney et al., (2004) "Activation of Resting Human Primary T Cells with Chimeric Receptors: Costimulation from CD28, Inducible Costimulator, CD134, and CD137 in Series with Signals from the TCR Chain", Journal of Immunology, 172, pp. 104-113.
Thomas et al. (2011), "Human T cells expressing affinity-matured TCR display accelerated responses but fail to recognize low density of MHC-peptide antigen", Blood 118, pp. 319-329.
Ma et al., "Chimeric antigen receptors based on low affinity mutants of Fc?RI re-direct T cell specificity to cells expressing membrane IgE (HYP5P.321)" The Journal of Immunology May 1, 2015 vol. 194, No. 1 Supplement 124.4 (publically available Apr. 3, 2015) pp. 1-2.

\* cited by examiner

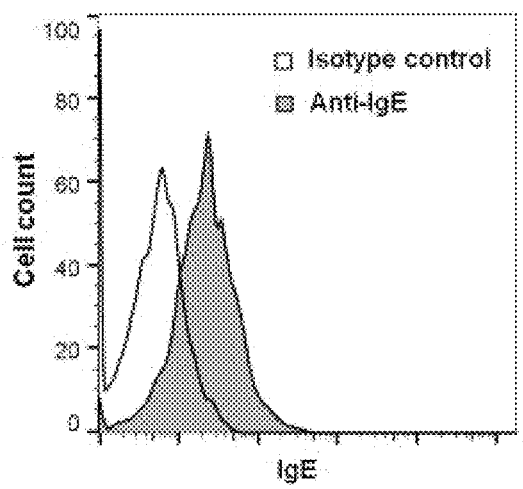
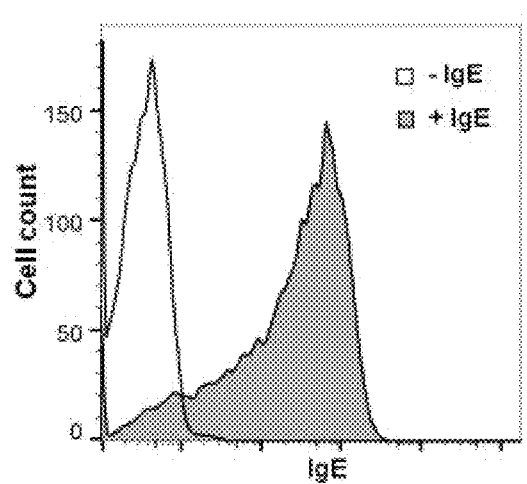
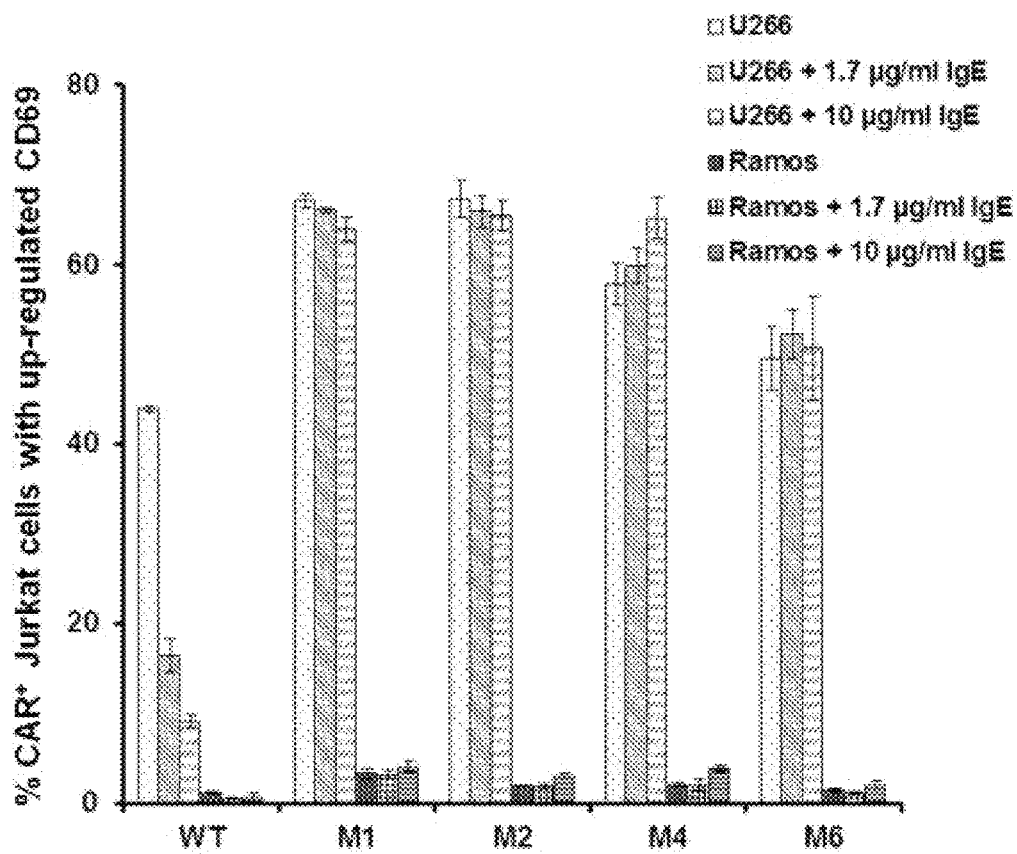

Fig. 6

```
  1 M  A  P  A  M  E  S  P  T  L  L  C  V  A  L  L  F  F  A  P    CD3ζ
  1 ATGGCTCCTGCCATGGAATCCCTACTCTACTGTGTGTAGCCTTACTGTTCTTCGCTCCA    signal pep.

21 D  G  V  L  A  V  P  Q  K  P  K  V  S  L  N  P  P  W  N  R
 61 GATGGCGTGTTAGCAGTCCCTCAGAAACCTAAGGTCTCCTTGAACCCTCCATGGAATAGA

41 I  F  K  G  E  N  V  T  L  T  C  N  G  N  N  F  F  E  V  S    FcεRIα
121 ATATTTAAAGGAGAGAATGTGACTCTTACATGTAATGGGAACAATTTCTTTGAAGTCAGT   extr.domain 61 S  T  K  W  F  H  N  G  S  L  S  E  E  T  N  S  S  L  N  I
181 TCCACCAAATGGTTCCACAATGGCAGCCTTTCAGAAGAGACAAATTCAAGTTTGAATATT 81 V  N  A  K  F  E  D  S  G  E  Y  K  C  Q  H  Q  Q  V  N  E
241 GTGAATGCCAAATTTGAAGACAGTGGAGAATACAAATGTCAGCACCAACAAGTTAATGAG 101 S  E  P  V  Y  L  E  V  F  S  D  W  L  L  L  Q  A  S  A  E    FcεRIαW87
301 AGTGAACCTGTGTACCTGGAAGTCTTCAGTGACTGGCTGCTCCTTCAGGCCTCTGCTGAG 121 V  V  M  E  G  Q  P  L  F  L  R  C  H  G  W  R  N  W  D  V
361 GTGGTGATGGAGGGCCAGCCCCTCTTCCTCAGGTGCCATGGTTGGAGGAACTGGGATGTG   FcεRIαW113

141 Y  K  V  I  Y  Y  K  D  G  E  A  L  K  Y  W  Y  E  N  H  N    FcεRIαK117
421 TACAAGGTGATCTATTATAAGGATGGTGAAGCTCTCAAGTACTGGTATGAGAACCACAAC   FcεRIαY131

161 I  S  I  T  N  A  T  V  E  D  S  G  T  Y  Y  C  T  G  K  V
481 ATCTCCATTACAAATGCCACAGTTGAAGACAGTGGAACCTACTACTGTACGGGCAAAGTG   FcεRIαV155

181 W  Q  L  D  Y  E  S  E  P  L  N  I  T  V  I  K  A  P  R  E    FcεRIαD159
541 TGGCAGCTGGACTATGAGTCTGAGCCCCTCAACATTACTGTAATAAAAGCTCCGCGTGAG

201 K  Y  W  L  Q  G  G  S  G  G  Q  S  F  G  L  L  D  P  K  L    linker
601 AAGTACTGGCTACAAGGTGGATCAGGAGGACAGAGCTTTGGCCTGCTGGATCCCAAACTC   CD3ζ extr.

221 C  Y  L  L  D  G  I  L  F  I  Y  G  V  I  L  T  A  L  F  L    CD3ζ transm.
661 TGCTACCTGCTGGATGGAATCCTCTTCATCTATGGTGTCATTCTCACTGCCTTGTTCCTG   domain 241 R  V  K  F  S  R  S  A  D  A  P  A  Y  Q  Q  G  Q  N  Q  L
721 AGAGTGAAGTTCAGCAGGAGCGCAGACGCCCCCGCGTACCAGCAGGGCCAGAACCAGCTC 261 Y  N  E  L  N  L  G  R  R  E  E  Y  D  V  L  D  K  R  R  G    CD3ζ intra.
781 TATAACGAGCTCAATCTAGGACGAAGAGAGGAGTACGATGTTTTGGACAAGAGACGTGGC   domain 281 R  D  P  E  M  G  G  K  P  Q  R  R  K  N  P  Q  E  G  L  Y
841 CGGGACCCTGAGATGGGGGGAAAGCCGCAGAGAAGGAAGAACCCTCAGGAAGGCCTGTAC 301 N  E  L  Q  K  D  K  M  A  E  A  Y  S  E  I  G  M  K  G  E
901 AATGAACTGCAGAAAGATAAGATGGCGGAGGCCTACAGTGAGATTGGGATGAAAGGCGAG 321 R  R  R  G  K  G  H  D  G  L  Y  Q  G  L  S  T  A  T  K  D
961 CGCCGGAGGGGCAAGGGGCACGATGGCCTTTACCAGGGTCTCAGTACAGCCACCAAGGAC 341 T  Y  D  A  L  H  M  Q  A  L  P  P  R
1021 ACCTACGACGCCCTTCACATGCAGGCCCTGCCCCCTCGC
```

ADOPTIVE T-CELL THERAPY USING FCεRI-BASED CHIMERIC ANTIGEN RECEPTORS FOR TREATING IGE-MEDIATED ALLERGIC DISEASES

CROSS-REFERENCE TO RELATED APPLICATION

This is a continuation-in-part of application Ser. No. 15/058,286, filed Mar. 2, 2016, now abandoned which claims the benefit of the filing date of U.S. Provisional Patent Application No. 62/127,024, filed Mar. 2, 2015. The entire disclosures of the aforesaid applications are incorporated herein by reference in their entireties.

REFERENCE TO GOVERNMENT GRANT

The invention was made with government support under grant nos. P20GM10346 and R21AI1119841 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 17, 2016 is named 45009_0044_01_US_540015_ST25 and is 37,563 bytes in size.

FIELD OF THE INVENTION

The invention relates to methods and compositions for the treatment of atopic diseases.

BACKGROUND OF THE INVENTION

An estimated 50 million, or one in five, Americans suffer from allergies. Food allergies cause more than 200 deaths each year, and costs estimated $4,184 annually for each child, or around $25 billion overall (Gupta et al., (2013), *JAMA Pediatr,* 167:1026-1031). In the U.S., asthma affects 25 million people. On an annual basis, asthma directly causes more than 3,300 deaths, indirectly contributes to an additional 7,000 deaths, and costs $56 billion. Approximately 10% of sufferers have severe asthma, which has the highest morbidity and mortality, and consumes over 50% of the health care expenditure attributed to asthma. Severe asthma patients require large doses of corticosteroids in combination with other potentially toxic medications and still may suffer serious symptoms and frequent life-threatening asthma attacks. As a result, severe asthma seriously affects quality of life. According to a 2009 survey of severe asthma conducted by the Asthma and Allergy Foundation of America (AAFA), over a third of patients had made at least 5 emergency department visits and 14% had visited emergency departments twenty times or more. Half of respondents did not consider their current medications effective, two-thirds disliked the cost, and 41% disliked the side-effects. Over half of respondents would prefer to have a "drug-free option" for their asthma (*Severe Asthma Survey*. Asthma and Allergy Foundation of America; 2009). Allergic immune responses trigger the disease in two thirds of patients with asthma and up to 50% of patients with severe asthma ("The ENFUMOSA cross-sectional European multicenter study of the clinical phenotype of chronic severe asthma", European Network for Understanding Mechanisms of Severe Asthma, *Eur Respir J.* 2003; 22(3):470-7).

Allergic reactions are initiated when allergens cross-link specific IgE antibodies bound to the high-affinity receptor FcεRI on mast cells, basophils and eosinophils, thereby triggering degranulation that results in release of inflammatory chemical mediators. IgE therefore plays a central role in allergic asthma and presents an attractive target for therapeutic intervention.

The only drug that targets IgE today is omalizumab (Xolair) for severe allergic asthma. Omalizumab is an IgE-specific humanized monoclonal antibody that depletes IgE. The drug, however, has a relatively short half-life of 1 to 4 weeks (Belliveau et al. (2005), *MedGenMed* 7:27) an therefore requires repeated administration at high doses (two 150 mg vials every four weeks for most adults), and costs close to $20,000 per year (Kochenderfer et al., (2010), *Blood* 116:4099-4102). A 2007 analysis concluded that omalizumab was not cost-effective for adults with severe asthma (Wu et al., *J Allergy Clin Immunol.* 2007; 120(5):1146-52).

Thus, better approaches for treatment of atopic diseases such as allergic asthma are required. In particular, an approach that persistently suppresses the IgE level over a long period of time with a single treatment would be highly desirable.

SUMMARY OF THE INVENTION

An isolated nucleic acid sequence encoding a chimeric antigen receptor (CAR) is provided, wherein the CAR comprises a human FcεRIα extracellular domain and an intracellular signaling domain comprising at least one immunoreceptor-based activation motif (ITAM). In some embodiments, the nucleic acid sequence further encodes a costimulatory signaling domain. In some embodiments, the encoded costimulatory domain comprises at least the intracellular domain of at least one of 4-1BB, CD27, CD28, CD134 or ICOS.

In an embodiment, an isolated nucleic acid sequence encoding a chimeric antigen receptor (CAR) is provided, wherein the CAR comprises a human FcεRIα extracellular domain; and a CD3ζ component comprising at least the intracellular domain of human CD3ζ; and optionally a costimulatory signaling region comprising the intracellular domain of human CD28 or human 4-1BB, or the intracellular domain of both human CD28 and human 4-1BB.

In certain embodiments, the isolated nucleic acid sequence encodes a chimeric antigen receptor (CAR) wherein the encoded CD3ζ component comprises a CD3ζ extracellular domain, a CD3ζ transmembrane domain, and a CD3ζ signaling domain. In some embodiments, the encoded CD3ζ extracellular domain has the amino acid sequence SEQ ID NO: 33. In some embodiments, the CD3ζ extracellular domain is encoded by the nucleotide sequence SEQ ID NO: 34. In some embodiments, the encoded CD3ζ transmembrane domain has the amino acid sequence SEQ ID NO: 11. In some embodiments, the CD3ζ transmembrane domain is encoded by the nucleotide sequence SEQ ID NO: 12. In some embodiments, the encoded CD3ζ signaling domain has the amino acid sequence SEQ ID NO: 5. In some embodiments, the CD3ζ signaling domain is encoded by the nucleotide sequence SEQ ID NO:6. In some embodiments, the entire CD3ζ component has the amino acid sequence SEQ ID NO: 13. In some embodiments, the entire CD3ζ component is encoded by nucleotide sequence SEQ ID NO: 14.

In certain embodiments, the isolated nucleic acid sequence encodes a chimeric antigen receptor (CAR) wherein the encoded FcεRIα extracellular domain is a mutant FcεRIα extracellular domain that has a reduced binding affinity for human IgE compared to wild type human FcεRIα extracellular domain. In certain embodiments, the isolated nucleic acid sequence encodes a chimeric antigen receptor (CAR) wherein the encoded mutant human FcεRIα extracellular domain has a binding affinity for human IgE characterized by a dissociation constant ($K_d$) of from $1\times10^{-4}$ to $1\times10^{-10}$ M, preferably from $1\times10^{-6}$ to $1\times10^{-9}$ M, more preferably from $1\times10^{-7}$ to $1\times10^{-8}$ M.

In certain embodiments, the isolated nucleic acid sequence encodes a chimeric antigen receptor (CAR), wherein the encoded mutant human FcεRIα extracellular domain comprises an amino acid sequence wherein at least one amino acid position is substituted with another amino acid compared to wild type human FcεRIα.

In certain embodiments, the isolated nucleic acid sequence encodes a chimeric antigen receptor (CAR) wherein the encoded mutant human FcεRIα extracellular domain comprises the amino acid sequence of SEQ ID NO: 1, wherein at least one amino acid position in SEQ ID NO: 1 is substituted with another amino acid.

In certain embodiments, the isolated nucleic acid sequence encodes a chimeric antigen receptor (CAR) wherein the encoded mutant human FcεRIα extracellular domain comprises the amino acid sequence of SEQ ID NO: 1, wherein from 1 to 6 amino acid positions in SEQ ID NO: 1 are substituted with another amino acid.

In certain embodiments, the isolated nucleic acid sequence encodes a chimeric antigen receptor (CAR) wherein the encoded mutant human FcεRIα extracellular domain comprises the amino acid sequence of SEQ ID NO: 1, wherein at least one of the following amino acid positions is substituted by another amino acid: Trp113, Lys1117, Val155 or Asp159. In certain embodiments, the isolated nucleic acid sequence encodes a chimeric antigen receptor (CAR) wherein the encoded mutant human FcεRIα extracellular domain comprises the amino acid sequence of SEQ ID NO: 1, with one of the following single or double mutations being present: Lys117Asp; Lys117Asp+Asp159Ala; Lys117Asp+Trp113Ala; or Lys117Asp; +Val155Ala.

In certain embodiments, the isolated nucleic acid sequence encodes a chimeric antigen receptor (CAR) wherein the encoded CAR comprises at its N-terminus a human CD3ζ signal peptide. In some embodiments, the CD3ζ signal peptide has the amino acid sequence SEQ ID NO: 7. In some embodiments, the CD3ζ signal peptide is encoded by the nucleotide sequence SEQ ID NO: 8.

In certain embodiments, the isolated nucleic acid sequence encoding the chimeric antigen receptor (CAR) comprises a nucleic acid sequence selected from the group consisting of the following: (a) SEQ ID NO: 28; (b) the contiguous sequence of nucleotides from nucleotide 76 to nucleotide 1059 of SEQ ID NO: 28; (c) SEQ ID NO: 20; (d) the contiguous sequence of nucleotides from nucleotide 76 to nucleotide 1059 of SEQ ID NO: 20; (e) SEQ ID NO: 22; (f) the contiguous sequence of nucleotides from nucleotide 76 to nucleotide 1059 of SEQ ID NO: 22; (g) SEQ ID NO: 24; (h) the contiguous sequence of nucleotides from nucleotide 76 to nucleotide 1059 of SEQ ID NO: 24; (i) SEQ ID NO: 26; and (j) the contiguous sequence of nucleotides from nucleotide 76 to nucleotide 1059 of SEQ ID NO: 26.

In certain embodiments, the isolated nucleic acid sequence encodes the chimeric antigen receptor (CAR) wherein the costimulatory signaling domain comprises the intracellular domain of CD28 or 4-1BB, or the intracellular domains of both CD28 and 4-1BB.

According to other embodiments, a chimeric antigen receptor (CAR) is provided comprising a human FcεRIα extracellular domain and an intracellular signaling domain comprising at least one immunoreceptor-based activation motif (ITAM). In some embodiments, the CAR further comprises a costimulatory signaling domain. In some embodiments, the costimulatory domain comprises at least the intracellular domain of at least one of 4-1BB, CD27, CD28, CD134 or ICOS.

In an embodiment, a chimeric antigen receptor (CAR) is provided, wherein the CAR comprises a human FcεRIα extracellular domain; and, a CD3ζ component comprising, at least the intracellular domain of human CD3ζ; and optionally a costimulatory signaling region comprising the intracellular domain of human CD28 or human 4-1BB, or the intracellular domain of both human CD28 and human 4-1BB.

In certain embodiments of the CAR, the CD3ζ component comprises a CD3ζ extracellular domain, a CD3ζ transmembrane domain, and a CD3ζ signaling domain. In some embodiments, the CD3ζ extracellular domain has the amino acid sequence SEQ ID NO: 33. In some embodiments, the CD3ζ extracellular domain is encoded by the nucleotide sequence SEQ ID NO: 34. In some embodiments, the CD3ζ transmembrane domain has the amino acid sequence SEQ ID NO: 11. In some embodiments, the CD3ζ transmembrane domain is encoded by the nucleotide sequence SEQ ID NO: 12. In some embodiments, the CD3ζ signaling domain has the amino acid sequence SEQ ID NO: 5. In some embodiments, the CD3ζ signaling domain is encoded by the nucleotide sequence SEQ ID NO:6. In some embodiments, the CD3ζ component has the amino acid sequence SEQ ID NO: 13. In some embodiments, the CD3ζ component is encoded by the nucleotide sequence SEQ ID NO: 14.

In certain embodiments, the FcεRIα extracellular domain is a mutant FcεRIα extracellular domain that has a reduced binding affinity for human IgE compared to wild type human FcεRIα extracellular domain. In certain embodiments, the mutant human FcεRIα extracellular domain has a binding affinity for human IgE characterized by a dissociation constant ($K_d$) of from $1\times10^{-4}$ to $1\times10^{-10}$ M, preferably from $1\times10^{-6}$ to $1\times10^{-9}$ M, more preferably from $1\times10^{-7}$ to $1\times10^{-8}$ M.

In certain embodiments of the CAR, the mutant human FcεRIα extracellular domain comprises an amino acid sequence wherein at least one amino acid position is substituted with another amino acid compared to wild type human FcεRIα.

In certain embodiments of the CAR, the mutant human FcεRIα extracellular domain comprises the amino acid sequence of SEQ ID NO: 1, wherein at least one amino acid position in SEQ ID NO: 1 is substituted with another amino acid.

In certain embodiments of the CAR, the mutant human FcεRIα extracellular domain comprises the amino acid sequence of SEQ ID NO: 1, wherein from 1 to 6 amino acid positions in SEQ ID NO: 1 are substituted with another amino acid.

In certain embodiments of the CAR, the mutant human FcεRIα extracellular domain comprises the amino acid sequence of SEQ ID NO: 1, wherein at least one of the following amino acid positions is substituted by another amino acid: Trp113, Lys117, Val155 or Asp159. In certain embodiments, of the CAR, the mutant human FcεRIα extracellular domain comprises the amino acid sequence of SEQ ID NO: 1, with one of the following single or double mutations being present: Lys117Asp; Lys117Asp+Asp159Ala; Lys117Asp+Trp113Ala; or Lys117-Asp; +Val155Ala.

In certain embodiments, the costimulatory signaling domain of the CAR comprises the intracellular domain of CD28 or 4-1BB, or the intracellular domains of both CD28 and 4-1BB.

In certain embodiments of the CAR, the CAR comprises at its N-terminus a human CD3ζ signal peptide. In some embodiments, the CD3ζ signal peptide has the amino acid sequence SEQ ID NO: 7. In some embodiments, the CD3ζ signal peptide is encoded by the nucleotide sequence SEQ ID NO: 8.

In certain embodiments, the CAR comprises an amino acid sequence selected from the group consisting of the following: (a) SEQ ID NO: 27; (b) the contiguous sequence of amino acids from amino acid 26 to amino acid 353 of SEQ ID NO: 27; (c) SEQ ID NO: 19; (d) the contiguous sequence of amino acids from amino acid 26 to amino acid 353 of SEQ ID NO: 19; (e) SEQ ID NO: 21; (f) the contiguous sequence of amino acids from amino acid 26 to amino acid 353 of SEQ ID NO: 21; (g) SEQ ID NO: 23; (h) the contiguous sequence of amino acids from amino acid 23 to amino acid 353 of SEQ ID NO: 23; (i) SEQ ID NO: 25; and (j) the contiguous sequence of amino acids from amino acid 26 to amino acid 353 of SEQ ID NO: 25.

According to other embodiments, a T cell is provided comprising a nucleic acid sequence encoding a chimeric antigen receptor (CAR), the CAR comprising a human FcεRIα extracellular domain, and an intracellular signaling domain comprising at least one immunoreceptor-based activation motif (ITAM). In some embodiments, the intracellular signaling domain further comprises a costimulatory signaling domain. In some embodiments, the costimulatory domain comprises at least the intracellular domain of at least one of 4-1BB, CD27, CD28, CD134 or ICOS. In some embodiments, the T cells so provided comprise isolated T cells.

In an embodiment, a T cell is provided comprising a nucleic acid sequence encoding a chimeric antigen receptor (CAR), wherein the CAR comprises a human FcεRIα extracellular domain; and a CD3ζ component comprising at least the intracellular domain of human CD3ζ; and optionally a costimulatory signaling region comprising the intracellular domain of human CD28 or human 4-1BB, or the intracellular domain of both human CD28 and human 4-1BB.

In certain embodiments of the T cell, the intracellular signaling domain is a CD3ζ component comprises a CD3ζ extracellular domain, a CD3ζ transmembrane domain, and a CD3ζ signaling domain. In some embodiments, the CD3ζ extracellular domain has the amino acid sequence SEQ ID NO: 33. In some embodiments, the CD3ζ extracellular domain is encoded by the nucleotide sequence SEQ ID NO: 34. In some embodiments, the encoded CD3ζ transmembrane domain has the amino acid sequence SEQ ID NO: 11. In some embodiments, the CD3ζ transmembrane domain is encoded by the nucleotide sequence SEQ ID NO: 12. In some embodiments, the CD3ζ signaling domain has the amino acid sequence SEQ ID NO: 5. In some embodiments, the CD3ζ signaling domain is encoded by the nucleotide sequence SEQ ID NO:6. In some embodiments, the entire CD3ζ component has the amino acid sequence SEQ ID NO: 13. In some embodiments, the entire CD3ζ component is encoded by nucleotide sequence SEQ ID NO: 14.

In certain embodiments of the T cell, the FcεRIα extracellular domain is a mutant FcεRIα extracellular domain that has a reduced binding affinity for human IgE compared to wild type human FcεRIα extracellular domain. In certain embodiments of the T cell, the mutant human FcεRIα extracellular domain has a binding affinity for human IgE characterized by a dissociation constant ($K_d$) of from $1\times10^{-4}$ to $1\times10^{-10}$ M, preferably from $1\times10^{-6}$ to $1\times10^{-9}$ M, more preferably from $1\times10^{-7}$ to $1\times10^{-8}$ M.

In certain embodiments of the T cell, the mutant human FcεRIα extracellular domain comprises an amino acid sequence wherein at least one amino acid position is substituted with another amino acid compared to wild type human FcεRIα.

In certain embodiments of the T cell, the mutant human FcεRIα extracellular domain comprises the amino acid sequence of SEQ ID NO: 1, wherein at least one amino acid position in SEQ ID NO: 1 is substituted with another amino acid.

In certain embodiments of the T cell, the mutant human FcεRIα extracellular domain comprises the amino acid sequence of SEQ ID NO: 1, wherein from 1 to 6 amino acid positions in SEQ ID NO: 1 are substituted with another amino acid.

In certain embodiments of the T cell, the mutant human FcεRIα extracellular domain comprises the amino acid sequence of SEQ ID NO: 1, wherein at least one of the following amino acid positions is substituted by another amino acid: Trp113, Lys117, Val155 or Asp159. In certain embodiments the T cell, the mutant human FcεRIα extracellular domain comprises the amino acid sequence of SEQ ID NO: 1, with one of the following single or double mutations being present: Lys117Asp; Lys117Asp+Asp159Ala; Lys117Asp+Trp113Ala; or Lys117Asp; +Val155Ala.

In certain embodiments of the T cell, the CAR comprises at its N-terminus a human CD3ζ signal peptide. In some embodiments, the CD3ζ signal peptide has the amino acid sequence SEQ ID NO: 7. In some embodiments, the CD3ζ signal peptide is encoded by the nucleotide sequence SEQ ID NO: 8.

In certain embodiments of the T cell, the CAR comprises an amino acid sequence selected from the group consisting of the following: (a) SEQ ID NO: 27; (b) the contiguous sequence of amino acids from amino acid 26 to amino acid 353 of SEQ ID NO: 27; (c) SEQ ID NO: 19; (d) the contiguous sequence of amino acids from amino acid 26 to amino acid 353 of SEQ ID NO: 19; (e) SEQ ID NO: 21; (f) the contiguous sequence of amino acids from amino acid 26 to amino acid 353 of SEQ ID NO: 21; (g) SEQ ID NO: 23; (h) the contiguous sequence of amino acids from amino acid 23 to amino acid 353 of SEQ ID NO: 23; (i) SEQ ID NO: 25; and (j) the contiguous sequence of amino acids from amino acid 26 to amino acid 353 of SEQ ID NO: 25.

In certain embodiments of the T cell, the costimulatory signaling domain comprises the intracellular domain of CD28 or 4-1BB, or the intracellular domains of both CD28 and 4-1BB.

According to other embodiments, a vector is provided comprising a nucleic acid sequence encoding a chimeric antigen receptor (CAR), wherein the CAR comprises a human FcεRIα extracellular domain and an intracellular signaling domain comprising at least one immunoreceptor-based activation motif (ITAM). In some embodiments, the nucleic acid sequence further encodes a costimulatory signaling domain. In some embodiments, the costimulatory domain comprises at least the intracellular domain of at least one of 4-1BB, CD27, CD28, CD134 or ICOS. In some embodiments, the vector so provided comprises an isolated vector.

In an embodiment, a vector is provided comprising a nucleic acid sequence encoding a chimeric antigen receptor (CAR), wherein the CAR comprises a human FcεRIα extracellular domain; a CD3ζ component comprising at least the intracellular domain of human CD3ζ; and optionally a costimulatory signaling region comprising the intracellular domain of human CD28 or human 4-1BB, or the intracellular domain of both human CD28 and human 4-1BB.

In certain embodiments of the vector, the nucleic acid sequence encodes a chimeric antigen receptor (CAR) wherein the encoded intracellular signaling domain is a CD3ζ component comprising a CD3ζ extracellular domain, a CD3ζ transmembrane domain, and a CD3ζ signaling domain. In some embodiments, the CD3ζ extracellular domain has the amino acid sequence SEQ ID NO: 33. In some embodiments, the CD3ζ extracellular domain is encoded by the nucleotide sequence SEQ ID NO: 34. In some embodiments, the encoded CD3ζ transmembrane domain has the amino acid sequence SEQ ID NO: 11. In some embodiments, the CD3ζ transmembrane domain is encoded by the nucleotide sequence SEQ ID NO: 12. In some embodiments, the encoded CD3ζ signaling domain has the amino acid sequence SEQ ID NO: 5. In some embodiments, the CD3ζ signaling domain is encoded by the nucleotide sequence SEQ ID NO:6. In some embodiments, the encoded CD3ζ component has the amino acid sequence SEQ ID NO: 13. In some embodiments, the CD3ζ component is encoded by nucleotide sequence SEQ ID NO: 14.

In certain embodiments of the vector, the encoded FcεRIα extracellular domain is a mutant FcεRIα extracellular domain that has a reduced binding affinity for human IgE compared to wild type human FcεRIα extracellular domain.

In certain embodiments of the vector, the encoded mutant human FcεRIα extracellular domain has a binding affinity for human IgE characterized by a dissociation constant ($K_d$) of from $1\times10^{-4}$ to $1\times10^{-10}$ M, preferably from $1\times10^{-6}$ to $1\times10^{-9}$ M, more preferably from $1\times10^{-7}$ to $1\times10^{-8}$ M.

In certain embodiments of the vector, the nucleic acid sequence encodes a chimeric antigen receptor (CAR) wherein the encoded mutant human FcεRIα extracellular domain comprises an amino acid sequence wherein at least one amino acid position is substituted with another amino acid compared to wild type human FcεRIα.

In certain embodiments of the vector, the nucleic acid sequence encodes a chimeric antigen receptor (CAR) wherein the encoded mutant human FcεRIα extracellular domain comprises the amino acid sequence of SEQ ID NO: 1, wherein at least one amino acid position in SEQ ID NO: 1 is substituted with another amino acid.

In certain embodiments of the vector, the nucleic acid sequence encodes a chimeric antigen receptor (CAR) wherein the encoded mutant human FcεRIα extracellular domain comprises the amino acid sequence of SEQ ID NO: 1, wherein from 1 to 6 amino acid positions in SEQ ID NO: 1 are substituted with another amino acid.

In certain embodiments of the vector, the nucleic acid sequence encodes a chimeric antigen receptor (CAR) wherein the encoded mutant human FcεRIα extracellular domain comprises the amino acid sequence of SEQ ID NO: 1, wherein at least one of the following amino acid positions is substituted by another amino acid: Trp113, Lys117, Val155 or Asp159. In certain embodiments of the vector, the nucleic acid sequence encodes a chimeric antigen receptor (CAR) wherein the encoded mutant human FcεRIα extracellular domain comprises the amino acid sequence of SEQ ID NO: 1, with one of the following single or double mutations being present: Lys117Asp; Lys117Asp+Asp159Ala; Lys117Asp+Trp113Ala; or Lys117Asp; +Val155Ala.

In certain embodiments of the vector, the nucleic acid sequence encodes a chimeric antigen receptor (CAR) wherein the costimulatory signaling domain of the CAR comprises the intracellular domain of CD28 or 4-1BB, or the intracellular domains of both CD28 and 4-1BB.

In certain embodiments of the vector, the nucleic acid sequence encodes a chimeric antigen receptor (CAR) wherein the encoded CAR comprises at its N-terminus a human CD3ζ signal peptide. In some embodiments, the CD3ζ signal peptide has the amino acid sequence SEQ ID NO: 7. In some embodiments, the CD3ζ signal peptide is encoded by the nucleotide sequence SEQ ID NO: 8.

In certain embodiments if the vector, the nucleic acid sequence encoding the chimeric antigen receptor (CAR) comprises a nucleic acid sequence selected from the group consisting of the following: (a) SEQ ID NO: 28; (b) the contiguous sequence of nucleotides from nucleotide 76 to nucleotide 1059 of SEQ ID NO: 28; (c) SEQ ID NO: 20; (d) the contiguous sequence of nucleotides from nucleotide 76 to nucleotide 1059 of SEQ ID NO: 20; (e) SEQ ID NO: 22; (f) the contiguous sequence of nucleotides from nucleotide 76 to nucleotide 1059 of SEQ ID NO: 22; (g) SEQ ID NO: 24; (h) the contiguous sequence of nucleotides from nucleotide 76 to nucleotide 1059 of SEQ ID NO: 24; (i) SEQ ID NO: 26; and (j) the contiguous sequence of nucleotides from nucleotide 76 to nucleotide 1059 of SEQ ID NO: 26.

According to other embodiments, a method for stimulating a T cell-mediated immune response to cells expressing mIgE in a subject is provided. The method comprises administering to the subject an effective amount of a T cells, according to any of the aforesaid T cell embodiments. In certain embodiments, the T cells comprise autologous T cells that are removed from the subject and engineered ex vivo to express the aforesaid chimeric antigen receptor (CAR) and administered to the subject.

According to other embodiments, a method for treating an IgE-mediated allergic disease in a subject in need of such treatment is provided. The method comprises administering to the subject an effective amount of T cells, according to any of the aforesaid T cell embodiments. According to another embodiment, a method of preventing an IgE-mediated allergic disease in a subject at risk of such disease is also provided. In certain embodiments of the aforesaid treatment and prevention methods, the T cells comprise autologous T cells that are removed from the subject and engineered ex vivo to express the aforesaid chimeric antigen receptor (CAR) and administered to the subject. In certain embodiments, the disease is selected from the group consisting of allergic asthma, food allergy, atopic dermatitis, allergic rhinitis, allergic rhinoconjunctivitis, chronic urticaria and systematic anaphylaxis.

Also provided are the aforesaid T cells for use in stimulating a T cell-mediated immune response to cells expressing mIgE in a subject. Also provided are the aforesaid T cells for treating an IgE-mediated allergic disease in a subject in need of such treatment, or for preventing an IgE-mediated allergic disease in a subject at risk of such disease. Also provided is a medicament or a pharmaceutical composition for use in stimulating a T cell-mediated immune response to cells expressing mIgE in a subject. Also provided is a medicament or a pharmaceutical composition for use in treating an IgE-mediated allergic disease, or for preventing an IgE-mediated allergic disease in a subject at risk of such disease.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DESCRIPTION OF THE FIGURES

FIG. 3A shows the U266 cells express low levels of mIgE. The cells were stained with anti-IgE-APC antibodies and analyzed by flow cytometry.

FIG. 3B shows that IL4-stimulated Ramos cells bind IgE at high levels. Ramos cells were stimulated with 20 ng/ml IL4 for three days to up-regulate FcεRII. The cells were incubated with 1.7 μg/ml IgE for 1 hr on ice, washed and stained with anti-IgE-APC antibodies.

FIG. 3C shows that CARs based on low affinity mutants of FcεRIα (FcεRIα') mediate specific T cell responses to mIgE+ target cells. Jurkat cells expressing CARs based on WT FcεRIα and the mutants M1, M2, M4, and M6 were tested for their responses to U266 and Ramos cells with or without IgE. For stimulation by U266 in the presence of free IgE, 0.125×10$^6$ U266 cells were incubated with 1.7 μg/ml or 10 μg/ml IgE for 15 minutes at 37° C., then an equal number of CAR$^+$ Jurkat cells were added. For stimulation with Ramos with bound IgE, Ramos cells stimulated as in FIG. B were incubated with 1.7 μg/ml or 10 μg/ml IgE for 1 hour on ice and washed. An equal number of CAR$^+$ Jurkat cells were added. The cells were incubated for 6 hours and CD69 expression was determined by flow cytometry. The data points are averaged values of triplicates with error bars representing standard deviation.

FIG. 6 is a representation of the nucleotide (SEQ ID NO: 28) and amino acid (SEQ ID NO: 27) sequences of an FcεRIα-based CAR showing representative amino acid positions in the wild type FcεRIα extracellular domain that may be mutated in forming low affinity CARs of the present invention. (The stop codon TAA has been removed from the 3'-terminus of the nucleotide sequence shown in FIG. 6). The FcεRIα extracellular domain is in bold. The positions for mutation in the extracellular domain are underlined: Trp87, Trp113, Lys117, Tyr131, Val155, Asp159. Numbering of the potential mutation sites is with respect to the beginning of the FcεRIα extracellular domain (Val at position 26 according to the marginal numbering). Upstream of the FcεRIα extracellular domain is a CD3ζ0 signal peptide (underlined). Downstream of the FcεRIα extracellular domain is a Gly-Gly-Ser-Gly-Gly linker (SEQ ID NO:3, dashed underline) connecting a CD3ζ component comprising a CD3ζ extracellular domain (double underlined), a CD3ζ transmembrane domain (underlined), and a CD3ζ intracellular domain comprising a CD3ζ signaling sequence. Results shown in FIG. 2 to FIG. 5 were obtained using CARs constructed in this configuration.

DEFINITIONS

Figure 1:
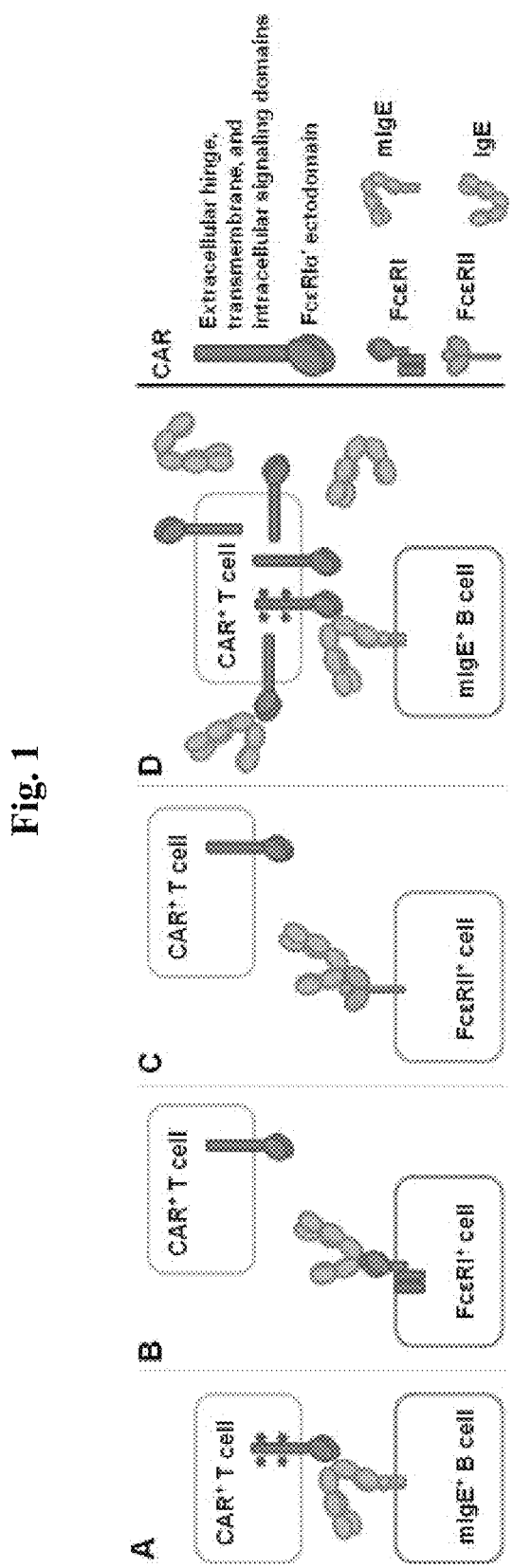
FIG. 1 is an illustration of the action of a CAR based on low affinity FcεRIα according to the present invention in redirecting T cell responses specifically to cells expressing mIgE. The elements of the figure are identified in the legend in the extreme right hand panel labeled "CAR". The CAR of the non-limiting embodiment shown in the figure includes the extracellular domain of a low affinity mutant of FcεRIα (FcεRIα') fused to an extracellular hinge, a transmembrane domain, and intracellular signaling domain. The and intracellular signaling domain contains at least one ITAM, and optionally one or more signaling domains of co-stimulatory molecules. Panel A shows the FcεRIα'-based CARs on a T cell (CAR$^+$ T cell), and the binding of mIgE and mediation of T cell responses to mIgE$^+$ cells. The IgE heavy chain assumes a bent conformation. The binding site for FcεRIα is at the bend. The binding triggers TCR signaling (shown as stars at the signaling domains), T cell activation and target cell killing. Panel B illustrates that the CAR$^+$ T cells do not recognize cells with IgE captured through FcεRI because IgE has only one FcεRI binding site. Panel C illustrates that the CAR$^+$ T cells do not recognize cells with IgE captured through FcεRII because IgE-FcεRII binding allosterically inhibits IgE-FcεRI binding. Panel D illustrates that the recognition of mIgE$^+$ target cells by a CAR$^+$ T cell can tolerate the presence of free IgE, even at relatively high concentrations. CARs on T cells will only be partially blocked by IgE because of the low affinity of FcεRIα'-IgE binding. The unoccupied CARs will still be able to recognize mIgE$^+$ on target cells, as shown in panel A.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type.

"About" as used herein when referring to a measurable value such as an amount, a temporal duration, and the like, is meant to encompass variations of +/−20% or +/−10%, more preferably +/−5%, even more preferably +/−1%, and still more preferably +/−0.1% from the specified value, as such variations are appropriate to perform the disclosed methods.

As used herein, the term "autologous" is meant to refer to any material derived from the same individual to which it is later to be re-introduced into the individual.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "fusion protein" or "fusion polypeptide" is a polypeptide comprised of at least two polypeptides and optionally a linking sequence, and that are operatively linked into one continuous protein. The two polypeptides linked in a fusion protein are typically derived from two independent sources (i.e., not from the same parental polypeptide), and therefore a fusion protein comprises two linked polypeptides not normally found linked in nature. Typically, the two polypeptides can be operably attached directly by a peptide bond, or may be connected by a linking group, such as a spacer domain. An example of a fusion polypeptide is a polypeptide that functions as a receptor for an antigen, wherein an antigen binding polypeptide forming an extracellular domain is fused to a different polypeptide, forming a "chimeric antigen receptor".

By "human FcεRIα extracellular domain" is meant not only a wild type human FcεRIα extracellular domain represented, for example, by the amino acid sequence SEQ ID NO: 1, but also mutants thereof having the functional characteristic of the wild type domain in binding IgE. Mutant FcεRIα extracellular domains may bind IgE to different degrees than wildtype FcεRIα extracellular domains, and are preferably characterized by a reduced binding affinity for human IgE compared to wild type human FcεRIα extracellular domains.

The term "signaling domain" refers to the functional portion of a protein which acts by transmitting information within the cell to regulate cellular activity via defined signaling pathways by generating second messengers or functioning as effectors by responding to such messengers.

By "IgE-mediated allergic disease" is meant an allergic disease caused, at least in part, by an IgE-mediated hypersensitivity reaction. Examples of such diseases include asthma, food allergy, atopic dermatitis, allergic rhinitis, allergic rhinoconjunctivitis, chronic urticaria and systematic anaphylaxis.

By "mutant" with respect to a polypeptide or portion thereof (such as a functional domain of a polypeptide) is meant a polypeptide that differs in amino acid sequence from the corresponding wild type polypeptide amino acid sequence by deletion, substitution or insertion of at least one amino acid. A "deletion" in an amino acid sequence or polypeptide is defined as a change in amino acid sequence in which one or more amino acid residues are absent as compared to the wild-type protein. As used herein an "insertion" or "addition" in an amino acid sequence or polypeptide is a change in an amino acid sequence that has resulted in the addition of one or more amino acid residues as compared to the wild-type protein. As an example, "mutant human FcεRIα extracellular domain" means the extracellular domain of FcεRIα wherein at least one amino acid is inserted, deleted or substituted in comparison to the corresponding wild type amino acid sequence. Preferably, the mutation comprises the substitution of one or more amino acids, preferably the substitution of 1, 2 or 3 amino acids. A greater number of substitutions is possible.

As used herein "substitution" in an amino acid sequence or polypeptide results from the replacement of one or more amino acids by different amino acids, respectively, as compared to the wild-type polypeptide.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "linker", also referred to as a "spacer" or "spacer domain" as used herein, refers to a an amino acid or sequence of amino acids that that is optionally located between two amino acid sequences in a fusion protein of the invention.

The term "hinge" or "hinge region" refers to a flexible polypeptide connector region providing structural flexibility and spacing to flanking polypeptide regions. The hinge can consist of natural or synthetic polypeptides.

The term "operably linked" (and also the term "under transcriptional control") refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to a human being.

The term "polynucleotide" is a chain of nucleotides, also known as a "nucleic acid". As used herein polynucleotides include, but are not limited to, all nucleic acid sequences which are obtained by any means available in the art, and include both naturally occurring and synthetic nucleic acids.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" means a DNA sequence recognized by the synthetic machinery of the cell, or introduced synthetic machinery, required to initiate the specific transcription of a polynucleotide sequence.

The term "transfected" or "transformed" or "transduced" means to a process by which exogenous nucleic acid is transferred or introduced into the host cell. A "transfected" or "transformed" or "transduced" cell is one which has been transfected, transformed or transduced with exogenous nucleic acid. The transfected/transformed/transduced cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Examples of vectors include but are not limited to, linear polynucleotides, polynucleotides associated with ionic or amphiphilic compounds, plasmids, and viruses. Thus, the term "vector" includes an autonomously replicating plasmid or a virus. The term is also construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Where any amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

DETAILED DESCRIPTION OF THE INVENTION

IgE is the key mediator of allergic diseases. In particular, IgE, and specifically the interaction of IgE with FcεRI, is central to the pathogenesis of allergy and asthma.

IgE has two known receptors, the high affinity receptor FcεRI and the low affinity receptor FcεRII (CD23). FcεRI is a natural IgE receptor, which consists of an α chain (FcεRIα) that binds to IgE Fc region with high affinity ($Kd \approx 10^{-10}$ M), and β and γ chains containing ITAM signaling domains. The other IgE receptor, FcεRII (CD23), exists as trimers and binds to MHC class II, integrins and CD21 in addition to IgE (Acharya et al., (2010) *Clin Exp Immunol* 162:12-23), making it unsuitable for CAR construction.

According to the present invention, IgE-expressing B cells, the source of IgE, are targeted using adoptive T cell therapy (ACT) to achieve long-term suppression of IgE. Autologous T cells are engineered to stably express chimeric antigen receptors (CARs) that are specific for IgE-expressing B cells ex vivo. The FcεRIα-based CAR design takes advantage of the natural and specific binding between FcεRI and IgE, and redirects T cell specificity to cells expressing mIgE, a transmembrane form of IgE. The ectodomain of the CAR on CAR+ T cells is formed by an FcεRIα extracellular domain which is either the wild type or a mutant having a lower affinity for binding IgE than the wildtype extracellular domain. The FcεRIα extracellular domain binds the target molecule mIgE. The CAR further comprises an intracellular signaling component serving as a an intracellular signaling (stimulating) domain of the CAR, an optional extracellular hinge, a transmembrane domain. The intracellular signaling component comprises at least one immunoreceptor tyrosine-based activation motif ("ITAM"). It may optionally further comprise one or more co-stimulatory domains. The intracellular signaling component functions for signaling and T-cell activation. In one embodiment, the stimulatory domain comprising the intracellular signaling domain derived from CD3ζ, for signaling and T-cell activation.

The activating signal provided by the intracellular signaling component is able to endow the CAR+ T-cells with the ability to lyse target cells and secret cytokines in response to antigen binding. By using low affinity mutants of FcεRI, the CAR design of the present invention can mediate specific T cell responses to mIgE+ cells by taking advantage of the specificity of FcεRI-IgE binding while avoiding issues associated with high affinity binding.

In one embodiment, a patient's T cells are isolated, expanded, and genetically modified to express FcεRIα-based chimeric antigen receptors (CARs), which enable T cell recognition of cells expressing the transmembrane form of IgE (mIgE), which is present on all IgE-producing B cells. The modified T cells are then transferred back to the patient to seek and destroy IgE-producing B cells, and thus source of IgE. The transferred cells develop a memory phenotype and continuously destroy newly emerged IgE-expressing cells. Previous studies using other types of T-cell therapy have shown that transferred T cells exhibit memory phenotype and persist for more than 10 years. For example, ACT using CD19-specific CARs led to complete remission in patients with B cell leukemia and lymphoma. See, e.g., Brentjens et al., (2013) *Sci Transl Med* 5:177ra138. Importantly, genetically modified T cells have been shown to persist for more than a decade in patients without adverse effects (Scholler et al., (2012) *Sci Transl Med* 4:132ra153), demonstrating the long term effectiveness and safety of ACT. It was estimated that a single CAR+ T cell is capable of killing more than 1000 target cells (Id.).

Thus, the present CAR-based adoptive T-cell therapy (ACT) approach for targeting IgE-expressing B cells is believed to be capable of providing long-term control or remission of IgE-mediated allergic diseases that may not be easily managed with currently available medications. Control of disease is achieved without the need for frequent administration, a disadvantage that limits to the range of applications of IgE monoclonal antibody therapy. Targeting the source of IgE, the IgE-expressing B cells, therefore, provides an attractive alternative to administration of IgE monoclonal antibodies.

The present CAR-based adoptive T-cell therapy (ACT) approach overcomes the limitations of monoclonal antibody based treatments, such as treatment with omalizumab, by eliminating the source of IgE production. IgE is produced by B cells that are class-switched with help from Th2 cells. IgE-expressing B cells go through different developmental stages that include germinal center B cells, plasmablasts, plasma cells, and memory B cells (Talay et al., (2012) *Nat Immunol* 13:396-404). These cells uniquely express mIgE on the cell surface that can be used as a molecular target. According to the present invention, T cells (preferably autologous T cells) are engineered to express a CAR that recognizes cells expressing mIgE. The engineering redirects T cell specificity to the mIgE-expressing cells, to destroy those cells.

The binding of the CAR to mIgE is sufficient to trigger T-cell receptor (TCR) signaling and target cell killing, since TCR triggering only requires low affinity ligand binding ($Kd \approx 1 \times 10^{-6}$ M) (FIG. 1, panel A). The CAR does not recognize cells with IgE captured on the surface through FcεRI because there is only one FcεRI binding site on IgE (FIG. 1, panel B). Also, the CAR does not recognize cells with IgE bound to FcεRII, since IgE-FcεRII binding allosterically inhibits IgE-FcεRI interaction (FIG. 1, panel C). In addition, the CAR is designed to work in the presence of free IgE because, due to its low affinity, it will not be easily blocked by free IgE through tight binding (FIG. 1, panel D). The CAR based on a low affinity mutant of FcεRIα can thus specifically redirect T cell killing to cells expressing mIgE.

FcεRIα Extracellular Domain

In some embodiments, the CAR comprises the wildtype FcεRIα extracellular domain, such as the domain represented by SEQ ID NO: 1, in lieu of a low IgE-affinity mutant thereof. While CARs comprising wildtype FcεRIα extracellular domains may be of lower potency and less tolerant for free IgE than CARs comprising low IgE-affinity FcεRIα extracellular domain mutants, the reduced potency may be therapeutically sufficient in some instances. Also, low tolerance to free IgE may be less of a disadvantage, depending on individual treatment conditions. For example, a patient may be pre-conditioned with a therapeutic agent, e.g., omalizumab, to deplete free IgE before CAR-based T-cell therapy is administered. Thus, in one embodiment, the patient is treated with CAR⁺ T-cells wherein the CAR comprises the wildtype FcεRIα extracellular domain, and the patient may be pre-conditioned before treatment by omalizumab to deplete free IgE.

In other embodiments, the CAR comprises a mutant FcεRIα extracellular domain having an amino acid sequence wherein at least one amino acid position is substituted with another amino acid compared to the corresponding compared to the corresponding FcεRIα extracellular domain wild type amino acid sequence. In certain embodiments, from 1 to 6, from 1 to 5, from 1 to 4, from 1 to 3, or from 1 to 2 amino acid positions are substituted. In preferred embodiments, 1 or 2 amino acids are substituted. In some embodiments, the mutant FcεRIα extracellular domain comprises the amino acid sequence SEQ ID NO: 1, wherein at least one amino acid position in SEQ ID NO: 1 is substituted with another amino acid. In certain embodiments, from 1 to 6, from 1 to 5, from 1 to 4, from 1 to 3, or from 1 to 2 amino acid positions of SEQ ID NO: are substituted. In preferred embodiments, 1 or 2 amino acids of SEQ ID NO: 1 are substituted. In certain embodiments, the one or more substitutions occur in a segment of SEQ ID NO: 1 from amino acid position 50 to amino acid position 180. In some embodiments, the one or more mutations occur in a segment of SEQ ID NO: 1 from amino acid position 80 to amino acid position 160. The number of amino acid position substituted in this segment, is preferably from 1 to 6, from 1 to 5, from 1 to 4, from 1 to 3, or from 1 to 2, with 1 or two being most preferred. In certain embodiments, the FcεRIα extracellular domain comprises the amino acid sequence of SEQ ID NO: 1, wherein at least one of the following amino acid positions are substituted by another amino acid: Trp113, Lys117, Val155 or Asp159. In some embodiments, the FcεRIα extracellular domain comprises the amino acid sequence of SEQ ID NO: 1, wherein at least one of the following mutations are present: Trp113Ala, Lys117Asp, Val155Ala or Asp159Ala. In some embodiments, the FcεRIα extracellular domain comprises the amino acid sequence of SEQ ID NO: 1, with one of the following single or double mutations being present: Lys117Asp; Lys117Asp+Asp159Ala; Lys117Asp+Trp113Ala; or Lys117Asp; +Val155Ala. The present invention also extends to nucleic acids encoding the CAR embodiments of this paragraph, vectors comprising said nucleic acids, and T cells expressing said CAR embodiments.

In some embodiments, the FcεRIα extracellular domain comprises an amino acid sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% amino acid sequence identity to SEQ ID NO:1.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator "http://blast (dot)ncbi(dot)nlm(dot)nih(dot)gov/Blast(dot)cgi". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAT) can be used.

Wildtype FcεRIα binds IgE with an affinity expressed as the dissociation constant of said binding ($K_d$) of $10^{-10}$ M. The low affinity mutant FcεRIα extracellular domains utilized in embodiments of the CAR are characterized by a reduced binding affinity for human IgE compared to wild type human FcεRIα extracellular domain. The low affinity mutant FcεRIα extracellular domains utilized in embodiments of the CAR bind IgE with a dissociation constant greater than $10^{-10}$ M. In some embodiments, the mutant FcεRIα extracellular domain binds IgE with a dissociation constant in the range of from $10^{-10}$ to $1 \times 10^{-4}$ M. In some embodiments, the dissociation constant is in the range of from $5 \times 10^{-10}$ to $1 \times 10^{-6}$ M; the range of $6 \times 10^{-10}$ to $1 \times 10^{-6}$ M; the range of $7 \times 10^{-10}$ to $1 \times 10^{-6}$ M; the range of $8 \times 10^{-10}$ to $1 \times 10^{-6}$ M; the range of $9 \times 10^{-10}$ to $1 \times 10^{-6}$ M; the range of $1 \times 10^{-9}$ to $1 \times 10^{-6}$ M; the range of $5 \times 10^{-9}$ to $1 \times 10^{-6}$ M; the range of $1 \times 10^{-8}$ to $1 \times 10^{-6}$ M; the range of $5 \times 10^{-8}$ to $1 \times 10^{-6}$ M; or the range of $1 \times 10^{-7}$ to $1 \times 10^{-6}$ M. In another embodiment, the dissociation constant is in the range of $1 \times 10^{-8}$ to $1 \times 10^{-7}$ M. In another embodiment, the dissociation constant is in the range of $1 \times 10^{-6}$ to $1 \times 10^{-4}$ M. In another embodiment, the dissociation constant is in the range of $10^{-10}$ to $1 \times 10^{-8}$ M.

The dissociation constant ($K_d$) is determined using a cell-based binding assay conducted at 25° C., as described by Hakimi et al. (1990), *J Biol Chem* 265:22079.

ITAM-Containing Intracellular Signaling Component

The CAR includes an intracellular signaling domain. The intracellular signaling domain comprises a functional signaling domain derived from a stimulatory molecule. The intracellular signaling domain communicates the primary activation signal to the T cell. A "stimulatory molecule," refers to a molecule expressed by a T cell that provides the primary cytoplasmic signaling sequence(s) that regulate primary activation of the TCR complex in a stimulatory way for at least some aspect of the T cell signaling pathway. The domain comprises at least one immunoreceptor tyrosine-based activation motif ("ITAM"). For a discussion of ITAM-containing polypeptides, see US Pat. Pub. 2015/0368342, particularly paragraphs 0175-0196 thereof. The entire disclosure of US Pat. Pub. 2015/0368342 is incorporated herein by reference. Examples of suitable ITAM-containing polypeptides include, but are not limited to: DAP12; FcεRIγ; CD3δ; CD3ε, CD3γ; CD3ζ; and CD79A. A preferred ITAM-containing polypeptide is CD3ζ.

An ITAM is $YX_1X_2L/I$, where $X_1$ and $X_2$ are independently any amino acid (SEQ ID NO:31). In some cases, the intracellular signaling domain of a CAR comprises 1, 2, 3, 4, or 5 ITAMs. In some cases, an ITAM is repeated twice in an intracellular signaling domain, where the first and second instances of the ITAM are separated from one another by 6 to 8 amino acids, e.g.: $(YX_1X_2L/I)(X_3)_n(YX_1X_2L/I)$, where n is an integer from 6 to 8, and each of the 6-8 $X_3$ can be any amino acid (SEQ ID NO:32). In some cases, the intracellular signaling domain of a CAR comprises 1 ITAM. In some cases, the intracellular signaling domain of a CAR comprises 3 ITAMs.

In certain embodiments, the intracellular signaling domain of the CAR can contain the entire amino acid sequence of an ITAM-containing polypeptide. See US Pat. Pub. 2015/0368342 for a description of the ITAM-containing polypeptides DAP12, FcεRI, CD3δ, CD3ε, CD3γ, CD3ζ and CD79A, including amino acid sequences of known isoforms, and identification of the contained ITAMs.

In other embodiments, the intracellular signaling domain for the CAR of the present invention may comprise an ITAM-containing portion of the corresponding full-length parent ITAM-containing intracellular signaling polypeptide. The ITAM-containing portions suitable as intracellular signaling domains in the CAR of the present invention are described in US Pat. Pub. 2015/0368342. In one embodiment, the intracellular signaling domain may comprise the intracellular domain of CD3ζ, said intracellular domain comprising amino acids 241-253 of the CAR shown in FIG. 6. The sequence of amino acids 241-253 of the CAR shown in FIG. 6 is SEQ ID NO: 5.

In some embodiments, the intracellular signaling domain comprises an amino acid sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% amino acid sequence identity to SEQ ID NO:5.

In one embodiment, the CAR employed in the present invention comprises the extracellular domain of a low affinity mutant of the natural IgE receptor, FcεRI, for mIgE recognition, combined with an intracellular signaling component comprising at least the intracellular domain of human CD3ζ, (i.e., the entire CD3ζ molecule or at least a portion thereof that contains the intracellular domain thereof) to generate a chimeric protein.

In one embodiment, the CAR comprises a human FcεRI extracellular domain (either the wildtype or a low affinity mutant of FcεRIα) and a CD3ζ component that includes the CD3ζ intracellular signaling domain (which includes an ITAM), and also the CD3ζ extracellular and transmembrane domains. Accordingly, the entire CD3ζ, arranged in the contiguous naturally occurring order from N-terminus to C-terminus of extracellular→transmembrane→intracellular may be attached to the C-terminus of the FcεRIα extracellular domain (either the wildtype or a low affinity mutant of FcεRIα), through an optional spacer domain, as shown in FIG. 6. In some embodiments, the CD3ζ extracellular domain has the amino acid sequence SEQ ID NO: 33. In some embodiments, the CD3ζ extracellular domain is encoded by the nucleotide sequence SEQ ID NO: 34. In some embodiments, the CD3ζ transmembrane domain has the amino acid sequence SEQ ID NO: 11. In some embodiments, the CD3ζ transmembrane domain is encoded by the nucleotide sequence SEQ ID NO: 12. In some embodiments, the CD3ζ intracellular signaling domain has the amino acid sequence SEQ ID NO: 5. In some embodiments, the CD3ζ intracellular signaling domain is encoded by the nucleotide sequence SEQ ID NO:6. In some embodiments, the entire CD3ζ component has the amino acid sequence SEQ ID NO: 13. In some embodiments, the entire CD3ζ component is encoded by the nucleotide sequence SEQ ID NO: 14.

Linkers/Spacers

Adjacent domains of the CAR may be connected by a linker domain, often referred to as a spacer or spacer domain. The linker is an oligo- or polypeptide, and may contain any variety of amino acid sequences. A linker can be a peptide of between about 2 and about 40 amino acids in length, between about 2 and about 25 amino acids in length, or between about 2 and about 10 amino acids in length. Linkers can be produced by using synthetic, linker-encoding oligonucleotides to couple the proteins. Peptide linkers with a degree of flexibility may be used. The use of small amino acids, such as glycine and alanine, are of use in creating a flexible peptide. The creation of such sequences is routine to those of skill in the art.

In one embodiment, the linker comprises a sequence of glycine and serine residues, e.g. the pentapeptide Gly-Gly-Ser-Gly-Gly (SEQ ID NO: 3). Other linker sequences known to those skilled in the art may be utilized. A representative nucleotide sequence encoding the spacer domain Gly-Gly-Ser-Gly-Gly is GGTGGATCAG GAGGA (SEQ ID NO: 4).

Transmembrane Domain; Hinge Region

The CAR may further comprise, C-terminal of the FcεRIα extracellular domain (or optional linker), a transmembrane domain. The transmembrane domain is disposed between the FcεRIα extracellular domain and the intracellular signaling component. Any transmembrane domain that provides for insertion of a polypeptide into the cell membrane of a eukaryotic (e.g., mammalian) cell is suitable for use.

In certain embodiments, the FcεRIα extracellular domain may be connected to the intracellular signaling component (comprising the intracellular signaling domain and optional co-stimulatory domain(s)) via a contiguous extracellular hinge region, the transmembrane domain, and an intracellular spacer. For a description of the construction of CARs see, for example, Shirasu et al. *Anticancer Res.* 2012; 32(6):2377-83, the entire disclosure of which is incorporated herein by reference.

The transmembrane domain, and also the extracellular hinge and intracellular spacer, may be derived either from a natural or from a synthetic source. Where the source is natural, the transmembrane domain, the extracellular hinge region and intracellular spacer may be derived, for example, from any membrane-bound or transmembrane protein, such as the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD8 or immunoglobulin heavy chain. The extracellular hinge region, transmembrane domain, and intracellular spacer may derived from the same transmembrane protein, or may comprise a combination of elements from different transmembrane proteins.

In one embodiment, the transmembrane domain is the CD3ζ transmembrane domain, and the intracellular signaling domain comprises the intracellular domain of CD3ζ. In another embodiment, the CAR comprises a transmembrane domain other than the native CD3ζ transmembrane domain, and a further spacer domain is incorporated between the transmembrane domain and the CD3ζ intracellular domain.

In one embodiment, the FcεRIα extracellular domain is connected to a CD3ζ. component comprising all or a portion of the extracellular domain of CD3ζ, the transmembrane domain of CD3ζ, and the intracellular domain of CD3ζ. The CD3ζ component is fused to the FcεRIα extracellular domain (or optional linker) as shown in FIG. 6.

Co-Stimulatory Domains

The CAR may optionally further comprise a co-stimulatory domain to provide a fully competent activation signal to the T cell on which the CAR is expressed. A costimulatory signaling domain refers to the intracellular portion of a costimulatory molecule. A "costimulatory molecule" refers to the cognate binding partner on a T cell that specifically binds with a costimulatory ligand, thereby mediating a costimulatory response by the T cell, such as, but not limited to, proliferation. The co-stimulatory signaling domain can comprise the entire intracellular portion, or the entire native intracellular signaling domain, of the molecule from which it is derived, or a functional fragment thereof. Thus, in certain embodiments, the co-stimulatory domain of the CAR may comprise at least the signaling (cytoplasmic) domain of one or more co-stimulatory molecules for enhanced T cell signaling. The co-stimulatory molecules are typically receptors. The key attribute of this dual-signaling is to confer greater strength of signaling and persistence to the T cells, resulting in overall greater potency.

A co-stimulatory domain can comprise an intracellular portion of a transmembrane protein. Non-limiting examples of suitable co-stimulatory polypeptides include, but are not limited to, 4-1BB (CD137), CD27, CD28, CD134, and ICOS. A co-stimulatory domain can have a length of from 30-70 amino acids. Larger and smaller co-stimulatory domains are also contemplated, such as from 70-200, or 70-100 amino acids, or even larger.

The co-stimulatory domain is derived, for example, from an intracellular portion of the transmembrane protein 4-1BB. In certain embodiments, the intracellular domain of 4-1BB comprises the amino acid sequence:

(SEQ ID NO: 15)
Lys Arg Gly Arg Lys Lys Leu Leu Tyr Ile Phe Lys

Gln Pro Phe Met Arg Pro Val Gln Thr Thr Gln Glu

Glu Asp Gly Cys Ser Cys Arg Phe Pro Glu Glu Glu

Glu Gly Gly Cys Glu Leu.

In certain embodiments, the aforementioned 4-1BB intracellular domain amino acid sequence is encoded by the nucleotide sequence:

(SEQ ID NO: 16)
AAACGGGGCA GAAAGAAACT CCTGTATATA TTCAAACAAC

CATTTATGAG ACCAGTACAA ACTACTCAAG AGGAAGATGG

CTGTAGCTGC CGATTTCCAG AAGAAGAAGA AGGAGGATGT

GAACTG.

The co-stimulatory domain may be derived, for example, from an intracellular portion of the transmembrane protein CD28. In certain embodiments, the intracellular domain of CD28 comprises the amino acid sequence:

(SEQ ID NO: 17)
Arg Ser Lys Arg Ser Arg Leu Leu His Ser Asp Tyr

Met Asn Met Thr Pro Arg Arg Pro Gly Pro Thr Arg

Lys His Tyr Gln Pro Tyr Ala Pro Pro Arg Asp Phe

Ala Ala Tyr Arg Ser.

In certain embodiments, the aforementioned CD28 amino acid sequence of SEQ ID NO: 17 is encoded by the nucleotide sequence:

(SEQ ID NO: 18)
AGGAGTAAGA GGAGCAGGCT CCTGCACAGT GACTACATGA

ACATGACTCC CCGCCGCCCC GGGCCCACCC GCAAGCATTA

CCAGCCCTAT GCCCCACCAC GCGACTTCGC AGCCTATCGC

TCC.

The co-stimulatory domain may be derived, for example, from an intracellular portion of the transmembrane protein ICOS. In certain embodiments, the intracellular domain of ICOS comprises the amino acid sequence:

(SEQ ID NO: 35)
Thr Lys Lys Lys Tyr Ser Ser Ser Val His Asp Pro

Asn Gly Glu Tyr Met Phe Met Arg Ala Val Asn Thr

Ala Lys Lys Ser Arg Leu Thr Asp Val Thr Leu.

The co-stimulatory domain may be derived, for example, from an intracellular portion of the transmembrane protein CD134. In certain embodiments, the intracellular domain of CD134 comprises the amino acid sequence:

(SEQ ID NO: 36)
Arg Arg Asp Gln Arg Leu Pro Pro Asp Ala His Lys

Pro Pro Gly Gly Gly Ser Phe Arg Thr Pro Ile Gln

Glu Glu Gln Ala Asp Ala His Ser Thr Leu Ala Lys

Ile.

The co-stimulatory domain may be derived, for example, from an intracellular portion of the transmembrane protein CD27. In certain embodiments, the intracellular domain of CD27 comprises the amino acid sequence:

(SEQ ID NO: 37)
His Gln Arg Arg Lys Tyr Arg Ser Asn Lys Gly Glu

Ser Pro Val Glu Pro Ala Glu Pro Cys Arg Tyr Ser

Cys Pro Arg Glu Glu Glu Gly Ser Thr Ile Pro Ile

Gln Glu Asp Tyr Arg Lys Pro Glu Pro Ala Cys Ser

Pro.

A suitable co-stimulatory domain may comprise an amino acid sequence having at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% amino acid sequence identity to any of the co-stimulatory molecule amino acid sequences noted above.

The intracellular signaling domain comprising the principal signaling portion containing an ITAM, and optional co-stimulatory domain(s), may be combined in any order.

Preferably, the co-stimulatory domain(s) are located N-terminal to the intracellular signaling domain, and is (are) connected to a transmembrane domain of the CAR directly or via a spacer. The ITAM-containing portion is located C-terminal of the co-stimulatory domain(s), and thus forms the C-terminal region of the CAR.

In certain embodiments, the CAR comprises as co-stimulatory domain the signaling domains of CD28 and/or 4-1BB. The proximity of CD28 and/or 4-1BB to the membrane has been shown to improve CAR surface expression (Geiger et al., *Blood* 2001; 98:2354-2371). The principal signaling portion of the intracellular signaling domain, containing the one or more ITAMs, and optional co-stimulatory domains, e.g. the CD28 and/or 4-1BB domains, may be separated by optional spacers of the type described above.

It has been demonstrated that the CD28 signaling region could be provided in the same construct in series with the TCR chain to enhance the activation of human T cells, and in the context of antitumor CAR+ T-cells, enhance tumor cell killing. The addition of costimulatory signaling domains increases the potential of transferred T cells to expand and persist in vivo. CAR$^+$ T cells transferred without prior host immunosuppression have been shown to persist for more than 11 years in humans (Scholler et al., *Sci Transl Med.* 2012; 4(132):132ra53). The cells can persist with a memory phenotype, which allows long term monitoring and elimination of target cells (Kalos et al., *Sci Transl Med.* 2011; 3(95):95ra73). In the context of CARs, the addition of CD28 sequences to CD3ζ chain-based receptors increases antigen-induced secretion of interleukin-2 (IL-2) and in vitro T-cell expansion, potently enhances T-cell receptor-induced proliferation and differentiation of naive T cells, especially at low T-cell receptor occupancy and enhances the expression of downstream regulators that impact on T-cell proliferation, death, differentiation, and effector functions, for hours or days after the initial T cell-antigen presenting cell (APC) encounter. See Zhong et al., *Molecular Therapy* (2010) 18 2, 413-420. Further addition of the cytoplasmic domain of 4-1BB has been shown to result in enhanced signaling. (Id.)

Signal Peptide.

The CAR may optionally and preferably comprise an N-terminal segment comprising a signal peptide. The nucleic acid construct encoding the CAR may contain, a nucleic acid segment encoding the signal sequence at the 5' terminus of the open reading frame (ORF), which signal sequence peptide directs the chimeric protein to the cell surface membrane. Since the signal sequence will be removed from the chimeric protein being processed while being directed to the surface membrane, the particular signal sequence will normally not be critical to the subject invention. In one embodiment, the signal sequence comprises the CD3ζ signal peptide, as shown in FIG. 6. In certain embodiments, the CD3ζ signal peptide comprises the amino acid sequence SEQ ID NO: 7,

```
                                    (SEQ ID NO: 7)
Met Ala Pro Ala Met Glu Ser Pro Thr Leu Leu Cys

Val Ala Leu Leu Phe Phe Ala Pro Asp Gly Val Leu

Ala .
``` and may be encoded by the nucleotide sequence SEQ ID NO: 8:

```
                                    (SEQ ID NO: 8)
ATGGCTCCTG CCATGGAATC CCCTACTCTA CTGTGTGTAG

CCTTACTGTT CTTCGCTCCA GATGGCGTGT TAGCA
```

The CD3ζ signal peptide is fused to the N-terminus of the FcεRIα extracellular domain, optionally through a spacer domain of the type described above.

The CAR may comprise further optional segments, such as extracellular hinge regions, and other signaling elements in addition to the signaling domain and optional co-stimulatory domains.

The components of CAR are thus arranged according to well-known principles. The architecture of CARs for adoptive immunotherapy of cancer is described, for example, in Shirasu et al. *Anticancer Res.* 2012; 32(6):2377-83, showing the arrangement of extracellular antigen-binding domain, hinge/spacer domain, transmembrane domain, intracellular singalling domain, and co-stimulatory domain(s).

Advantage of the FcεRIα-Based CAR

The FcεRIα-based CAR of the present invention advantageously satisfies certain critical requirements for Adoptive T Cell Therapy targeting mIgE-expressing cells. The FcεRIα-based CAR bind mIgE with appropriate strength to trigger T cell activation. TCR signaling is normally triggered by low affinity ligand binding ($K_d \approx 10^{-6}$ M) (Krogsgaard et al., *Mol Cell.* 2003; 12(6):1367-78), and CARs that bind ligands with $K_d$ from $10^{-6}$ M to $10^{-9}$ M have been shown to function effectively as anti-tumor CARs (Turatti et al., *J Immunother.* 2007; 30(7):684-93). FcεRIα-based CAR containing low affinity mutant FcεRIα ectodomains are particularly useful in this regard, in view of their low affinity for IgE.

FcεRIα mutants of a wide range of affinities for mIgE can be evaluated for suitability as a CAR. The CARs of the present invention satisfy this requirement.

As described in the Examples, CAR with wild type FcεRIα was able to mediate T cell responses to U266 cells expressing low levels of mIgE (FIG. 3C). The level of T cell response, however, was relatively low, and it was inhibited by the presence of free IgE. Without wishing to be bound by any theory, the high affinity binding between WT CAR and mIgE likely prevented serial triggering of CARs by low density mIgE on U266 cells. It has been postulated that for T cells to respond to low density ligands, serial triggering of multiple T cell receptors by individual ligands is necessary for T cell activation through signal accumulation. Without wishing to be bound by any theory, the high affinity binding between WT CAR and free IgE likely prevented binding between CARs and mIgE on U266 cells. A large proportion of the CARs on T cells were likely blocked by tightly bound IgE, unable to interact with mIgE on the surface of target cells.

In contrast, the low affinity CARs of the present invention bind mIgE with sufficient strength to trigger activating signals, without binding too strongly for mIgE to serially trigger CARs. Therefore, the low affinity CARs mediated stronger T cell responses to U266 cells (FIG. 3C). Without wishing to be bound by any theory, in the presence of secreted IgE at a certain concentrations, T cells expressing low affinity CARs of the present invention are likely to have a smaller proportion blocked by IgE binding than T cells expressing the WT CAR. Without wishing to be bound by any theory, this should attribute to the low affinity CARs' tolerance of secreted IgE at concentrations as high as 1.7 μg/ml.

The CARs of the present invention based on low affinity FcεRIα mutants mediate robust T cell responses to cells expressing low levels of mIgE (FIG. 3C). Primary T cells engineered to express low affinity FcεRI-based CARs mediated robust T cell response in terms of cytokine production and killing of target cells expressing low levels of mIgE (FIGS. 5B, 5C)

The high sensitivity of these CARs to mIgE indicates that all IgE$^+$ cells may be targeted, including plasma cells that express mIgE at low levels. T cell responses to mIgE$^+$ cells mediated by low affinity FcεRI-based CARs tolerate free IgE at high concentrations (FIG. 3C and FIG. 5B) The ability of these low affinity CARs to tolerate high concentrations of secreted IgE is highly desirable, since IgE levels in the microenvironment surrounding the IgE-producing cells is likely much higher than in serum.

Figure 4A:
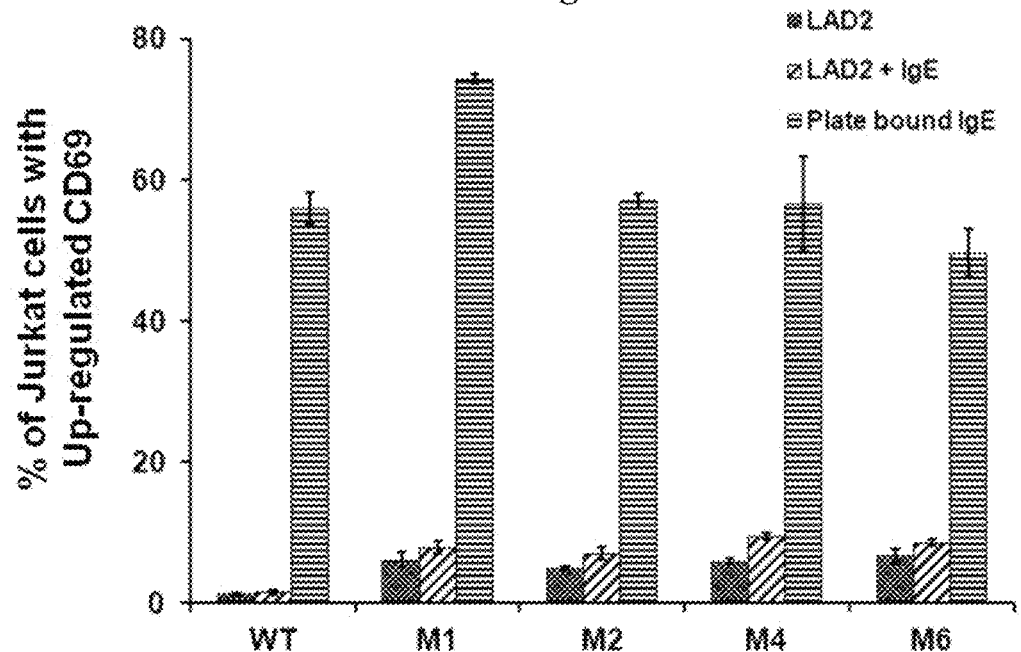
FIG. 4A shows that FcεRIα'-based CARs do not mediate T cell responses to mast cells with free IgE captured through FcεRI, or mediate mast cell activation. LAD2 cells were incubated with 1.7 μg/ml of IgE to bind with the FcεRI receptors on surface. The cells were then used to stimulate CAR$^+$ Jurkat T cells for 5 hours. The up-regulation of CD69 was determined by flow cytometry. LAD2 cells not treated with IgE were used as negative controls. The data represent the mean values of triplicate samples and standard deviation.
Figure 4B:
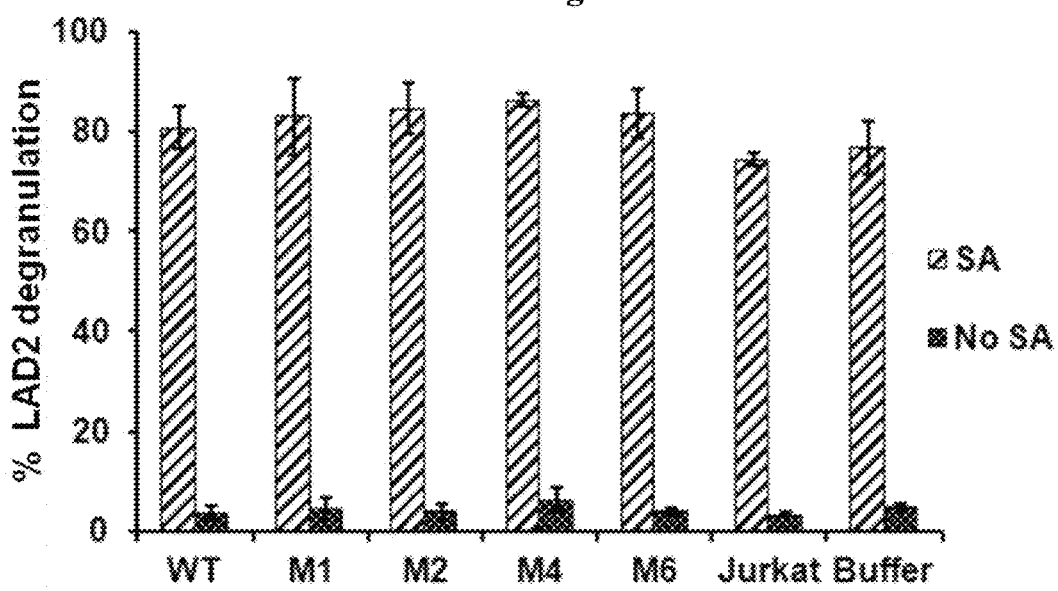
FIG. 4B shows that FcεRIα'-based CARs do not mediate mast cell activation. LAD2 cells were coated with biotinylated IgE at 1.7 μg/ml followed by incubation with CAR$^+$ Jurkat T cells for 30 minutes in the presence or absence of streptavidin. β-Hexosaminidase was determined using PNAG as substrate, and the percentage of degranulation was calculated. The data represent the mean values of triplicate samples and standard deviation.

IgE may exist on cell surfaces in three different forms: mIgE, IgE bound to FcεRI, and IgE bound to FcεRII. To avoid off-target killing of cells expressing FcεRI and FcεRII, a CAR directed against IgE-secreting cells should not recognize IgE bound to FcεRI or FcεRII. This goal is achieved by the CAR of the present invention. The FcεRIα-based CAR utilized in the practice of the invention would not recognize secreted IgE bound to FcεRI on the cell surface, since IgE has only one FcεRI binding site (Garman et al., *Nature* 2000; 406(6793):259-66), thus preventing CAR$^+$ T cells from targeting FcεRI$^+$ mast cells, eosinophils, basophils and Langerhans cells (Katona et al., *J Immunol.* 1983; 130(1):350-6; Kraft et al., *Nat Rev Immunol.* 2007; 7(5): 365-78). This prevents CAR$^+$ T cells according to the present invention from killing these cells or activating them by crosslinking surface IgE. This is supported by the Examples below, which demonstrate that LAD2 mast cells with IgE bound through FcεRI did not activate CAR$^+$ Jurkat cells (FIG. 4A), and that LAD2 cells did not degranulate when co-cultured with CAR$^+$ Jurkat cells (FIG. 4B).

The majority of B cells express FcεRII and its binding to IgE regulates IgE production (Gould et al., (2003) *Annu Rev Immunol* 21:579-628). FcεRII is also expressed on a variety of inflammatory cells and epithelial cells. It is therefore important that FcεRI-based CARs do not mediate off-target T cell responses to these cells though interaction with IgE captured on FcεRII. A CAR directed against IgE-secreting cells should thus not recognize IgE bound to FcεRII on cell surfaces. This goal is achieved by the CAR of the present invention. Although FcεRI and FcεRII bind IgE at distinct sites, FcεRI-IgE binding requires an Fc conformation that is not compatible with FcεRII-IgE binding, and vice versa (Dhaliwal et al., *Proc Natl Acad Sci USA.* 2012; 109(31): 12686-91). As a result, the two bindings allosterically inhibit each other. The FcεRIα-based CAR therapy of the invention takes advantage of this reciprocal allosteric inhibition between IgE-FcεRI and IgE-FcεRII bindings to prevent nonspecific targeting of cells with secreted IgE captured on the surface, a key roadblock in ACT targeting of mIgE$^+$ cells. The FcεRIα-based CARs of the invention do not bind IgE that is already bound to FcεRII, preventing CAR$^+$ T cells from targeting FcεRII$^+$ B cells and other cell types such as germinal center follicular dendritic cells. This is confirmed by the Examples below, where it is demonstrated that CAR+ Jurkat cells engineered according to the present invention did not respond to Ramos cells with high levels of IgE bound through FcεRII (FIG. 3C).

Thus, it is believed that T cells expressing FcεRIα-based CARs according to the present invention will not target cells expressing FcεRI or FcεRII and cause undesirable side effects in ACT. However, any minor off-target killing of cells expressing FcεRI or FcεRII and blocking CARs on T cells, can be ameliorated or eliminated by administration of omalizumab to decrease or deplete IgE before ACT treatment. Preconditioning patients with omalizumab therefore should increase the effectiveness and safety of the ACT of the present invention.

mIgE recognition by the CAR will tolerate the presence of secreted IgE. Secreted IgE in circulation and tissues could bind CARs on the T cells and block their interaction with mIgE on the target cells. A low affinity FcεRIα such as used in an embodiment of the invention, however, alleviates this problem. At a given concentration of secreted IgE, a T cell expressing low affinity CARs will have a smaller proportion of CARs bound (blocked) by secreted IgE than a cell expressing high affinity CARs. For example, the upper limit of patient serum IgE levels for omalizumab treatment is 700 IU/ml or $8.75 \times 10^{-9}$ M, which would block 96% of CARs with wild type FcεRIα, but less than 1% of CARs with a low affinity FcεRIα' of $Kd=10^{-6}$ M on a T cell.

It is believed that the effectiveness of the therapy of the present invention, which targets IgE-expressing B-cells, is enhanced by the comparative accessibility of the relevant target cells, as compared to targeting of tumor cells. Tumor cells tend to reside in an immunosuppressive microenvironment. IgE class-switch and affinity maturation takes place in respiratory tract mucosa, suggesting that IgE-expressing B cells and plasma cells originate from mucosal tissues. In the nasal mucosa of patients with rhinitis, around 4% of the B cells and 12-19% of the plasma cells express IgE, whereas IgE expressing plasma cells in the bone marrow are comparably sparse, suggesting that IgE-expressing B cells are concentrated in mucosal tissues. As the first line of defense, mucosal tissues experience frequent infection-related inflammation, which should attract infiltration of T cells, including CAR$^+$ T cells targeting mIgE$^+$ according to the present invention. Moreover, allergic responses mediated by locally produced IgE, e.g. the release of inflammatory mediators by mast cells, should attract the CAR$^+$ T cells to target IgE-expressing cells.

The ACT approach described herein advantageously targets only IgE-expressing B cells, which makes up a very small fraction of total B cells. In normal individuals, serum IgE concentration is 10,000 to 100,000 times lower than IgG (Gould et al. (2003), *Annu Rev Immunol* 21:579-628). It is thus believed that the IgE-specific approach of the present invention should not significantly impact overall humoral immunity, which is mediated mostly by IgG antibodies.

The operation of an embodiment of the invention is illustrated in FIG. 1. FIG. 1 schematically illustrates the action of a CAR based on FcεRIα according to the present invention in redirecting T cell responses specifically to cells expressing mIgE. The extracellular domain of a low affinity mutant of FcεRIα (FcεRIα') is fused to an extracellular hinge, a transmembrane domain and an intracellular signaling domain(s) comprising one or more ITAMs and optional co-stimulator domains. FcεRIα'-based CARs on a T cell (CAR$^+$ T cell) bind mIgE and mediate T cell responses to mIgE$^+$ cells (Panel A). IgE heavy chain contains one more domain than that of IgG. The IgE heavy chain assumes a bent conformation and the binding site for FcεRIα resides at the bend. This geometry is believed to facilitate the binding of mIgE by CARs on T cells. The binding triggers TCR signaling (shown as stars at the signaling domains), T cell activation and target cell killing. CAR$^+$ T cells do not recognize cells with IgE captured through FcεRI because IgE has only one FcεRI binding site (Panel B). The CAR$^+$ T cells do not recognize cells with IgE captured through FcεRII because IgE-FcεRII binding allosterically inhibits IgE-FcεRI binding (Panel C). The recognition of mIgE+ target cells by a CAR+ T cell can tolerate the presence of free IgE at relatively high concentrations (Panel D). CARs on T cells will only be partially blocked by IgE because of the low affinity of FcεRIα'-IgE binding. The unoccupied CARs will still be able to recognize mIgE+ on target cells as in Panel A.

Generation of Low Affinity FcεRIα Mutants for CAR Construction

FcεRIα mutants for use in the practice of the invention may be readily obtained by known methods of mutagenesis. Previous mutagenesis studies have identified multiple low affinity FcεRIα mutants (Cook et al., *Biochemistry.* 1997; 36(50):15579-88; Hulett et al., *J Biol Chem.* 1999; 274(19): 13345-52). Additional mutants may be readily generated by routine mutagenesis methods known to those skilled in the art. One such method of mutagenesis is described by Cook et al., supra. Briefly, cDNA encoding the human FcεRIα subunit is obtained by RT-PCR from KU812 cells (ECACC, Porton Down, U.K). Truncated cDNA encoding the two extracellular domains (Val1 to Lys176, numbering according to Blank et al. (1989) *Nature* 337, 187-189) is obtained from the full-length cDNA by PCR using the two primers (forward) 5'-GCG CGC AAG CTT CGC CGC CAC CAT GGC TCC TGC CAT GG-3' (SEQ ID NO: 29) and (reverse) 5'-GCG CGC GAA TTC ATC ACT TCT CAC GCG GAG CT-3' (SEQ ID NO: 30). This product is then cloned as a HinDIII/EcoRI fragment into the pEE12 expression vector (Bebbington et al., (1992) *Biotechnology* 10, 169-175) to give the pEE12/sFcεRIα construct. Site-directed mutagenesis of sFcεRIα cDNA is then carried out using circular pEE12/sFcεRIα as the template for PCR mutagenesis of the sFcεRIα. This may be done using the splice overlap extension method based on that of Ho et al. (1989) *Gene* 77, 51-59. This method requires the use of two primers per mutation, one in the sense direction and the other in the antisense direction. See Cook et al., *Biochemistry.* 1997; 36(50):15579-88 for a description of representative primers. Mutagenesis may be based on the known crystal structure of the FcεRIα-IgE complex, which has revealed FcεRIα residues critical for IgE binding (Garman et al., *Nature.* 2000; 406(6793):259-66), incorporated herein by reference. A CAR based on low affinity FcεRIα mutant enables T cell specific recognition of mIgE+ B cells in the presence of relatively high concentrations of free IgE. It should be appreciated that the FcεRIα mutants for construction of the CARs of the present invention may be characterized by single or multiple mutations.

The generation of low affinity FcεRIα mutants for CAR construction resulted in six mutants, based on the wild type FcεRIα extracellular domain having the amino acid sequence SEQ ID NO: 1, which may be encoded by the nucleotide sequence SEQ ID NO: 2. The six mutants are as follows, with fold affinity reduction over wild type identified in parentheses: K117D (27×), D159A (2×), Y131A (3×), W113A (5×), W87D (7×), V155A (10×).

Nucleic Acid Constructs and Vectors

The present invention is also directed to DNA constructs encoding the CAR, where the nucleic acid sequences of the FcεRIα extracellular domain, ITAM-containing intracellular signaling component and optional co-stimulatory domains, e.g. CD28 and/or 4-1BB signaling elements, and other optional elements are operably linked. A chimeric construct encoding the various nucleotide sequences encoding the CAR components may be directly synthesized or prepared by well-known molecular biology techniques, from naturally derived or synthetically prepared nucleic acids encoding the components. The chimeric constructs, which encode the CAR of the invention may be prepared using natural sequences. The natural genes may be isolated and manipulated, as appropriate, so as to allow for the proper joining of the various domains. Thus, one may prepare the truncated portion of the sequence by employing polymerase chain reaction (PCR) using appropriate primers which result in deletion of the undesired portions of the gene. Alternatively, one may use primer repair where the sequence of interest may be cloned in an appropriate host. In either case, primers may be employed which result in termini which allow for annealing of the sequences to result in the desired open reading frame encoding the CAR protein. Thus, the sequences may be selected to provide for restriction sites which are blunt-ended. or have complementary overlaps. Preferably, the constructs are prepared by overlapping PCR.

In embodiments of the invention, the nucleic acid sequences for representative CARs containing, in 5'-3' order, a CD3ζ signal peptide, a FcεRIα' extracellular domain, a Gly-Gly-Ser-Gly-Gly spacer domain, and a CD3ζ component comprising the CD3ζ extracellular domain, the CD3ζ transmembrane domain, and the CD3ζ signaling domain are listed in Table 1 as follows. All components, except for the spacer domain, are derived from human proteins:

TABLE 1

| Nucleotide Sequence | Amino Acid Sequence | Site of FcεRIα extracellular domain mutation(s), if present |
| --- | --- | --- |
| 28 | 27 | wild type |
| 20 | 19 | Lys117Asp |
| 22 | 21 | Lys117Asp + Asp159Ala |
| 24 | 23 | Lys117Asp + Trp113Ala |
| 26 | 25 | Lys117Asp; + Val155Ala |

[1]Numbering of the mutation location is with regard to the commencement of the FcεRIα extracellular domain in the listed amino acid sequences, which is the Val at position 76 of SEQ ID NOs: 19, 21, 23 and 25.

The present invention is also directed to vectors in which the DNA of the invention is inserted. Vectors derived from retroviruses are preferred, as they provide long-term gene transfer since and allow stable integration of a transgene and its propagation in daughter cells. Expression of nucleic acids encoding the CARs of the invention may be achieved using well-known molecular biology techniques by operably linking a nucleic acid encoding the CAR to a promoter, and incorporating the construct into a suitable expression vector. The vectors can be suitable for replication and integration in eukaryotes. Typical cloning vectors contain transcription and translation terminators, initiation sequences, and promoters useful for regulation of the expression of the desired nucleic acid sequence.

As the target cell for CAR expression is a T cell, the expression vector is most preferably a lentivirus. In one embodiment, lentiviral vectors encoding CARs are produced according to current good manufacturing practices using a three-plasmid production approach, as original described by Zuufrey et al., *Nat. Biotechnol.* 15, 871-875 (1997), the entire disclosure of which is incorporated herein by reference. Briefly, to package lentiviruses, 293T human embryonic kidney epithelial cells are transfected with the transfer plasmid encoding the CAR, the multiply deleted packaging plasmid, and the plasmid encoding the envelope glycoprotein VSVg. After 24 hours, the lentiviral vectors are harvested by concentrating the culture supernatant through ultracentrifugation.

The CAR+ T cells of the invention can be generated by introducing a lentiviral vector containing a nucleic acid construct encoding the desired CAR into T cells, such as autologous T cells of a patient to be treated for an IgE-mediated allergic disease. A composition comprising autologous T cells is collected from a patient in need of such treatment. The cells are engineered into CAR+ T cells ex vivo, activated and expanded using the methods described herein and known in the art, and then infused back into the patient. The CAR+ T cells replicate in vivo resulting in persistent immunity against cells expressing mIgE.

T cells for genetic modification to express the CARs are obtained from a subject. Sources and methods for collecting, purifying, processing and storing T cells for genetic modification, are described, for example, in paragraphs 00173-00182 of US2013/0287748 A1. The entire disclosure of US2013/0287748 A1 is incorporated herein by reference. Briefly, T cells can be obtained from peripheral blood mononuclear cells, bone marrow, lymph node tissue, cord blood, thymus tissue, tissue from a site of infection, ascites, pleural effusion, spleen tissue, and tumors. Preferably, T cells are obtained from a unit of blood collected from a subject using any number of techniques known to those skilled in the art. Isolation of T cells may proceed according to procedures known in the art, as described in US2013/0287748 A1. The harvested T cells are then expanded using methods well-known in the art, such as described in US2013/0287748 A1.

According to one embodiment, T-cells are harvested and processed for lentiviral transduction as follows. Patient peripheral blood mononuclear cells are purified and washed in phosphate-buffered saline (PBS) with 1% human serum albumin. Lymphocytes are enriched using magnetic bead depletion of monocytes, according to known methods. Lymphocytes are cultured according to Good Manufacturing Practice regulations as previously described by Levine et al., (1998), *J Hematother* 7:437-448. The cells are expanded ex vivo for 14 days in a serum-free hematopoietic cell medium, e.g., X-VIVO 15 of Lonza Group Ltd. (a chemically defined, serum-free hematopoietic cell medium) supplemented with 10% Normal Human AB Serum, and then processed for reinfusion on day 14 of culturing. The magnetic beads are removed using a magnetic cell separation system. The cells are harvested, washed and resuspended in a Plasmalyte A containing 1% human serum albumin.

The processed T cells are then transduced with lentiviral vectors as described above to generate CAR+ T cells for administration. Transduction is carried out according to known protocols. For example, the cells are transduced with lentiviral vectors by mixing with the concentrated vectors and 8 µg/ml polybrene, spun at 2500 RPM for 90 minutes, and incubating in the 37° C. incubator for 24 hours.

Administration of CAR+ T Cells

The CAR+ T cells are administered to a subject in need of treatment for an IgE-mediated allergic disease, or a subject at risk of developing an IgE-mediated allergic disease. The CAR+ T are able to replicate in vivo, providing long-term persistence that can lead to sustained allergic disease control. The CAR+ T may be administered either alone, or as a pharmaceutical composition in combination with one or more pharmaceutically acceptable carriers, diluents or excipients and/or with other components, such as cytokines or other cell populations. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions are preferably formulated for intravenous administration. Preferably, the T cells comprise autologous T cells that are removed from the subject and engineered ex vivo to express the CAR and administered to the subject.

IgE-mediated allergic diseases that may be treated or prevented according to the present invention include, by way of example and not limitation, allergic asthma, food allergy, atopic dermatitis, allergic rhinitis, allergic rhinoconjunctivitis, chronic urticaria and systematic anaphylaxis.

The CAR+ T cells or pharmaceutical composition thereof may be administered by a route that results in the effective delivery of an effective amount of cells to the patient for pharmacological effect. Administration is typically parenteral. Intravenous administration is the preferred route, using infusion techniques that are commonly known in immunotherapy (see, e.g., Rosenberg et al., *New Eng. J. of Med.* 319:1676, 1988). The quantity of CAR+ T cells and frequency of administration are determined by such factors as the condition of the patient, and the type and severity of the patient's disease, although appropriate dosages may be determined by clinical trials. An "effective amount" is determined by a physician with consideration of individual differences in age, weight, disease state, and disease severity of the patient. Generally, the amount of CAR+ T given in a single dosage will range from about $10^6$ to $10^9$ cells/kg body weight, including all integer values within those ranges. The CAR+ T may be administered multiple times at these dosages. The optimal dosage and treatment regime for a particular patient can readily be determined by one skilled in the art of medicine by monitoring the patient for signs of disease and adjusting the treatment accordingly.

The practice of the invention is illustrated by the following non-limiting examples.

EXAMPLE 1

CAR Construction and Expression on T Cells
A. Materials: Cells and Antibodies

Jurkat cells (clone E6-1, ATCC TIB-152) an immortalized line of T lymphocyte cells, human B-lymphocyte U266 cells (ATCC TIB-196) and Ramos cells (clone 2G6.4C10, ATCC CRL-1923) were all obtained from ATCC. Jurkat T cells are used as model T cells because they can be easily transduced with lentiviral vectors and their activation can be assayed based on CD69 up-regulation and IL2 production. Jurkat cells have been used in previous studies on CAR design (James et al., *J Immunol.* 2008; 180(10):7028-38; Bridgeman et al., *J Immunol.* 2010; 184(12):6938-49; Thomas et al., *Blood.* 2011; 118(2):319-29). Jurkat, U266 and Ramos cell cells were cultured in RPMI medium containing 10% BSA. Cells of the human mast cell line LAD2 (Kirhenbuam et al. (2003), *Leuk. Rs.* 27:677-682) were kindly provided by D. Metcalfe and cultured in complete StemPro-34 serum free medium (Invitrogen) supplemented with 100 ng/ml of SCF (Peprotech). Fluorescently labeled antibodies for human FcεRIα, FcεRII (CD23), CD69, CD117 and IgE were from Biolegend. Purified human IgE was from Abcam. IgE was biotinylated using NHS-PEG4-bio (Pierce) for degranulation assays.

B. CAR Design and Construction

The plasmid pcDL-huFcεRIα containing DNA encoding human FcεRIα was obtained from Addgene (Cambridge, Mass.). The extracellular domain has the amino acid sequence SEQ ID NO: 1, encoded by the nucleotide sequence SEQ ID NO: 2. Jurkat cells were cultured in RPMI medium containing 10% BSA. Human CD3ζ cDNA was cloned from the Jurkat cells using RT-PCR. A wild type CAR (WT CAR) was constructed by fusing the FcεRIα extracellular domain to the N-terminus of ζ using overlapping PCR. The WT CAR has the amino acid sequence SEQ ID NO: 27, and the nucleotide sequence SEQ ID NO: 28.

The FcεRIα extracellular domain was mutated using PCR to generate six low affinity mutants: M1 (K117D), M2 (K117D+D159A), M3 (K117D+Y131A), M4 (K117D+W113A), M5 (K117D+W87D) and (K117D+V155A). The mutant FcεRIα extracellular domains were fused to CD3ζ via a Gly-Gly-Ser-Gly-Gly spacer domain (SEQ ID NO: 3) using overlapping PCR to generate mutant CARs. The nucleotide and amino acid sequences of four of the mutant CARS is shown in Table 2.

TABLE 2

| Nucleotide Sequence | Amino Acid Sequence | CAR designation | Cite of FcεRIα extracellular domain mutation(s)[1] |
|---|---|---|---|
| 20 | 19 | M1 | Lys117Asp |
| 22 | 21 | M2 | Lys117Asp + Asp159Ala |
| 24 | 23 | M4 | Lys117Asp + Trp113Ala |
| 26 | 25 | M6 | Lys117Asp; + Val155Ala |

[1]Numbering of the mutation location is with regard to the commencement of the FcεRIα extracellular domain in the listed amino acid sequences, which is the Val at position 76 of SEQ ID NOs: 19, 21, 23 and 25.

C. CAR Expression on Jurkat Cells

Figure 2A:
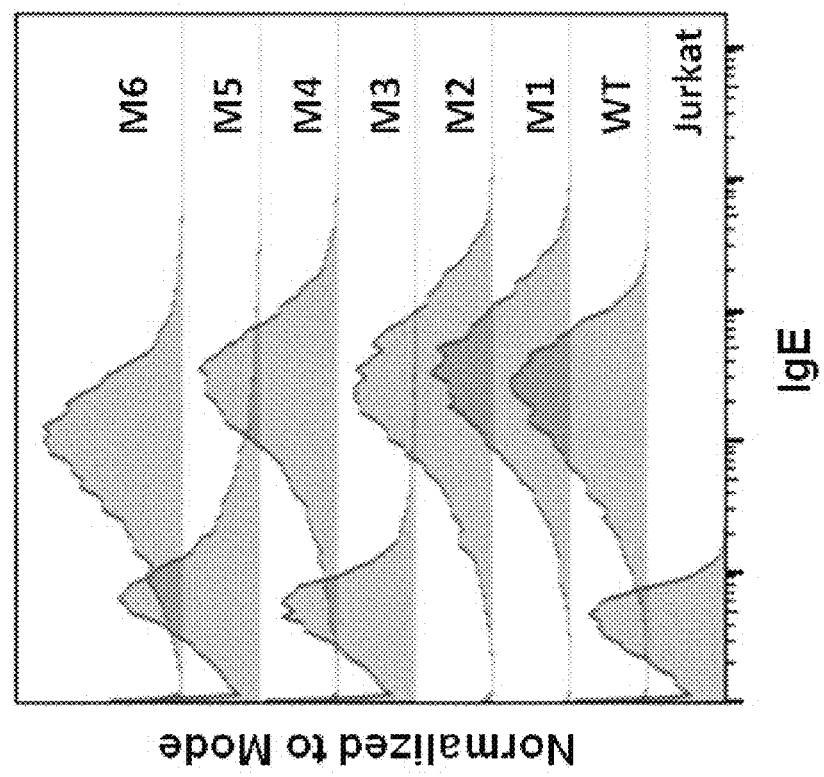
FIG. 2A shows Jurkat T cell expression of low affinity FcεRIα-based CARs. Jurkat cells transduced with lentiviral vectors for CARs based on wild type (WT) or six low affinity mutant FcεRIα (FcεRIα') (M1 through M6) were selected in medium containing puromycin. Cells were stained with anti-FcεRIα-PE antibody for flow cytometry. Untransduced Jurkat cells were used as a negative control.

DNA encoding WT or mutant CARs were inserted into the pLVX-EF1α-IRES-Puro lentiviral transfer vector (Clontech). Lentiviruses were generated from 293T cells using the Lenti-X packaging system (Clontech). Jurkat T cells were transduced with the lentiviruses using RetroNectin (Clontech), and selected in media containing 0.25 µg/ml puromycin. The expression of CARs on cell surface was determined by staining with anti-human FcεRI-PE antibodies for flow cytometry. Untransduced Jurkat was used as a control. The results are shown in FIG. 2A. The transduced Jurkat cells stably expressed the WT CAR and six mutant CARs at similar levels (FIG. 2A).

Figure 2B:
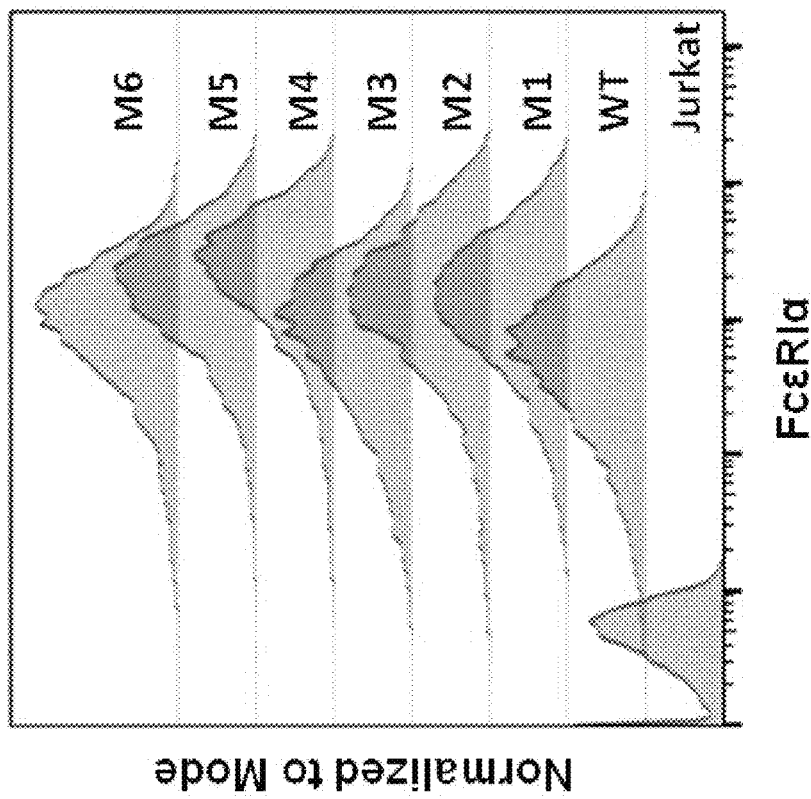
FIG. 2B shows the binding of IgE by the same transduced Jurkat cells of FIG. 2A. Jurkat cells of FIG. 2A were incubated with 10 μg/ml human IgE on ice for 1 hour, washed and stained with anti-IgE-APC antibody for flow cytometry.

To confirm the IgE-binding function, Jurkat cells expressing WT CAR were incubated with 10 µg/ml human IgE on ice for 1 hour, washed and stained with anti-IgE-APC antibody for flow cytometry. The results are shown in FIG. 2B. Jurkat cells expressing WT M1, M2, M4 and M6 (but not M3 and M5) CARs bound IgE (FIG. 2B), demonstrating the IgE-binding function of the FcεRIα component in the CAR.

D. CAR Expression on Jurkat Cells.

On Day 0, $10^6$ Primary human CD8+ T cells were stimulated with magnetic beads coated with anti-CD3ζ and anti-CD28 antibodies in a 48 well plate. On Day 1, 150 µl of concentrated pLVX-EF1α-IRES-Puro lentiviral transfer vector containing the M2 CAR sequence were added to the cells. Polybrene was also added to the final concentration of 8 µg/ml. The plate was then spun at 2500 RPM at 32° C. for 90 minutes. On day 2, half of the medium was removed and changed with fresh media and recombinant human IL2 was added to the final concentration of 50 unit/ml. On Day 4, the beads were removed using a magnet and the cells were cultured in fresh media containing IL2. The cells were analyzed for CAR expression and responses to target cells between Day 7 and Day 12.

EXAMPLE 2

Methods
A. Stimulation of CAR+ Jurkat Cells with U266 Cells, Ramos Cells, and LAD2 Cells.

Jurkat cells expressing CARs based on WT FcεRIα and the mutants M1, M2, M4, and M6 were tested for their responses to stimulation with U266 cells, Ramos cells or LAD2 cells. U266 is a human myeloma line that expresses low levels of mIgE (FIG. 3A), and is used to mimic mIgE+ plasma cells. Ramos cells are human B lymphocytes derived from an American Burkitt lymphoma. Ramos cells stimulated by IL4 to express FcεRII at appropriate levels and are used to mimic B cells expressing FcεRII. IL4-stimulated Ramos cells bind to IgE at high levels (FIG. 3B). LAD2 mast cells express FcεRI at levels comparable to primary mast cells and display robust FcεRI-induced degranulation (Guhl et al., *Exp Dermatol.* 2010; 19(9):845-7).

For stimulation by these cells, $0.125 \times 10^6$ Jurkat cells were mixed with equal number of U266, Ramos, or LAD2 cells in 200 al of medium, incubated for 5 hours at 37° C., stained with anti-FcεRI-PE plus CD69-APC (for U266 and Ramos cells), or anti-CD117-PE plus CD69-APC (for LAD2 cells), and analyzed using flow cytometry. To upregulate FcεRII, Ramos cells were stimulated with 20 ng/ml human IL4 (Peprotech) for 72 hrs. To bind IgE, IL4-stimulated Ramos cells were incubated with IgE of different concentrations for 1 hour on ice, washed, and IgE binding was confirmed with flow cytometry using IgE-specific antibodies.

A LAD2 cell degranulation assay, based on a previously published protocol by Kuehn et al (2010) *Curr. Protoc. Immunol.* 91:7.38.1-7.38.9, was employed with minor modifications. LAD2 cells were cultured in medium containing IgE-bio overnight. After washing with assay buffer (DPBS containing 10 mM HEPES, 5.6 mM glucose and 0.04% BSA, pH 7.4), 20,000 LAD2 cells were incubated with $2 \times 10^5$ CAR+ Jurkat cells in a 96 well plate at 37° C. for 30 minutes. The activities of β-hexosaminidase secreted to the supernatant and remained in the cells were determined using N-acetyl-β-D-glucosamide (PNAG) (Sigma) as substrate. As positive controls, streptavidin (1 µg/ml) was added to the LAD2-Jurkat mixture. The β-hexosaminidase activity from Jurkat cells were determined in control samples with Jurkat cells alone, and subtracted from the assay results. The percentage degranulation was calculated as 100×(supernatant activity)/(supernatant activity+lysate activity).

B. Stimulation of M2 CAR+ Human CD8+ T Cells with CD3/CD28 Beads and U266 Cells.

$0.125 \times 10^6$ untransduced human CD8+ T cells or human CD8+ T cells transduced with the M2 CAR were stimulated with equal numbers of beads coated with anti-CD3ζ and anti-CD28 antibodies, U266 cells, or U266 cells in the presence of 10 µg/ml free IgE. The cells were incubated for 24 hours and the IFNγ concentrations in the supernatant were measured using an ELISA kit (Biolegend).

C. U266 Cell Killing by M2 CAR+ Human CD8+ T Cells.

To generate U266 cells stably expressing luciferase (U266-luci), DNA sequences encoding the fire fly luciferase were inserted into pLVX-EF1α-IRES-Puro lentiviral transfer vector (Clontech). Lentiviral vectors were generated by transfecting 393T cells to transduce U266 cells. The U266-luci cells were selected by culturing in media containing puromycin. For the killing assay, 50,000 U266-luci cells were cultured with 150,000 CAR+ human CD8+ T cells, untransduced control T cells, or no T cells in a 96 well plate for 20 hours. The cells were harvested and the luciferase activities of the live cells were assayed using a Bright-Glo Luciferase Assay System (Promega). The level of bioluminescence reflecting the luciferase activity was measured for 1 second for each well using a Victor X plate reader (PerkinElmer) and recorded as relative light units (RLUs). The percentage of specific lysis was calculated from the data using the following equation: % specific lysis=100×[1−(T cell RLU/no T cell RLU)].

Results

A. FcεRI-based CARs Mediate Potent Jurkat T Cell Responses to mIgE+ Cells.

Jurkat cells expressing CARs based on WT FcεRIα and the mutants M1, M2, M4, and M6 were tested for their responses to stimulation by U266, a human myeloma line expressing low levels of mIgE (FIG. 3A). Equal numbers of U266 cells and CAR+ Jurkat cells were mixed.

Jurkat cells with WT, M1, M2, M4, and M4 CARs significantly up-regulated CD69 when stimulated with U266 cells (FIG. 3C). The WT CAR mediated the lowest response, consistent with reports that very high affinity TCR-ligand binding actually hinders T cell responses to low density ligands (Thomas et al. (2011), *Blood* 118:319-329). These results showed that FcεRIα-based CARs can mediate robust T cell responses to mIgE+ target cells, and the low affinity versions are more efficient than wild type.

B. T Cell Responses Mediated by Low Affinity FcεRI-based CARs Tolerate Secreted IgE.

Secreted IgE may impair the function of FcεRI-based CARs by binding to the CARs and blocking their interaction with mIgE on target cells. To test how well the CARs tolerate free IgE, CAR+ Jurkat cells were stimulated with U266 cells in the presence of 1.7 µg/ml or 10 µg/ml IgE for 15 min at 37° C. The IgE concentration of 1.7 µg/ml, or 700 IU/ml, is the upper limit of serum IgE level for omalizumab prescription.

As shown in FIG. 3C, 1.7 µg/ml IgE suppressed CD69 up-regulation by U266 cells more than 2-fold. IgE at 10 µg/ml suppressed more than 4-fold. In contrast, free IgE at this concentration did not significantly affect the low affinity CARs M1, M2, M4 and M6. Therefore, T cell responses to mIgE+ cells mediated by low affinity FcεRI-based CARs tolerate free IgE at high concentrations.

C. FcεRI-based CARs do not Mediate T Cell Responses to Secreted IgE Captured on Cells Through FcεRII The majority of B cells express FcεRII and its binding to IgE regulates IgE production (Gould et al., (2003) *Annu Rev Immunol* 21:579-628). FcεRII is also expressed on a variety of inflammatory cells and epithelial cells. It is therefore important that FcεRI-based CARs do not mediate off-target T cell responses to these cells though interaction with IgE captured on FcεRII. To test this, the 2G6.4C10 clone of Ramos Burkitt lymphoma cell that highly up-regulates FcεRII in response to IL4 stimulation was used. As shown in FIG. 3B, after stimulation with 20 ng/ml IL4 for three days, the Ramos cells bound IgE at high levels. As shown in FIG. 3C, Ramos cells coated with 1.7 µg/ml or 10 µg/ml IgE did not induce significant CAR+ Jurkat T cell response in terms of CD69 upregulation. Therefore, FcεRI-based CARs do not recognize cells with IgE captured via FcεRII.

D. FcεRI-based CARs do not Mediate T Cell Responses to Mast Cells with Secreted IgE Captured Through FcεRI, or Mediate Mast Cell Activation Secreted IgE is captured by FcεRI on the surface of mast cells, eosinophils, basophils and Langerhans cells. It is critical that T cells with FcεRI-based CARs do not target these cells or induce their degranulation and the release of inflammatory mediators. To test T cell responses, LAD2 mast cells were pulsed by incubation with 1.7 µg/ml of IgE to bind with FcεRI surface receptors (data not shown). The pulsed cells were then used to stimulate CAR+ Jurkat cells for 5 hours. The up-regulation of CD69 was determined by flow cytometry. LAD2 cells not treated with IgE were used as negative controls. As shown in FIG. 4A, Jurkat cells expressing WT, M1, M2, M4 and M6 CARs did not show significant CD69 up-regulation.

To determine whether CAR+Jurkat cells activate mast cells, LAD2 cells were pulsed by coating with biotinylated IgE at 1.7 µg/ml, and were co-cultured with CAR+Jurkat cells, control Jurkat cells, or buffer alone for 30 minutes in the present or absent of streptavidin. The release of β-hexosaminidase was measured as readout for degranulation. The β-hexosaminidase was determined using PNAG as substrate. A percentage of degranulation was calculated. As shown in FIG. 4B, in the presence of streptavidin, which crosslinks FcRεI by binding to the biotinylated IgE, a high percentage of degranulation (>70%) was induced. In the absence of streptavidin, however, only background levels of degranulation were observed. Taken together, Jurkat T cells expressing FcεRI-based CARs do not respond to, or activate mast cells with captured IgE through FcεRI.

E. The Low Affinity M2 CAR Mediates Specific Human CD8+ T Cell Responses to U266 Cells.

Figure 5A:
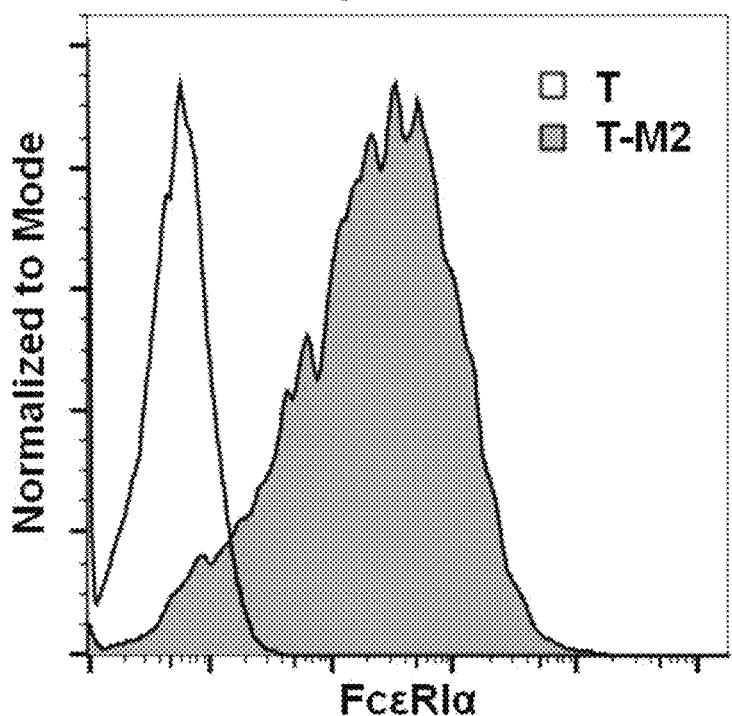
FIG. 5A shows the expression of low affinity M2 CAR on primary human CD8+ T cells. Purified human CD8+ T cells were transduced with lentiviral vectors encoding the M2 CAR. Cells were stained with anti-FcεRIα-PE antibody and analyzed by flow cytometry 7 days after the transduction. Untransduced human CD8+ T cells were used as a negative control.
Figure 5B:
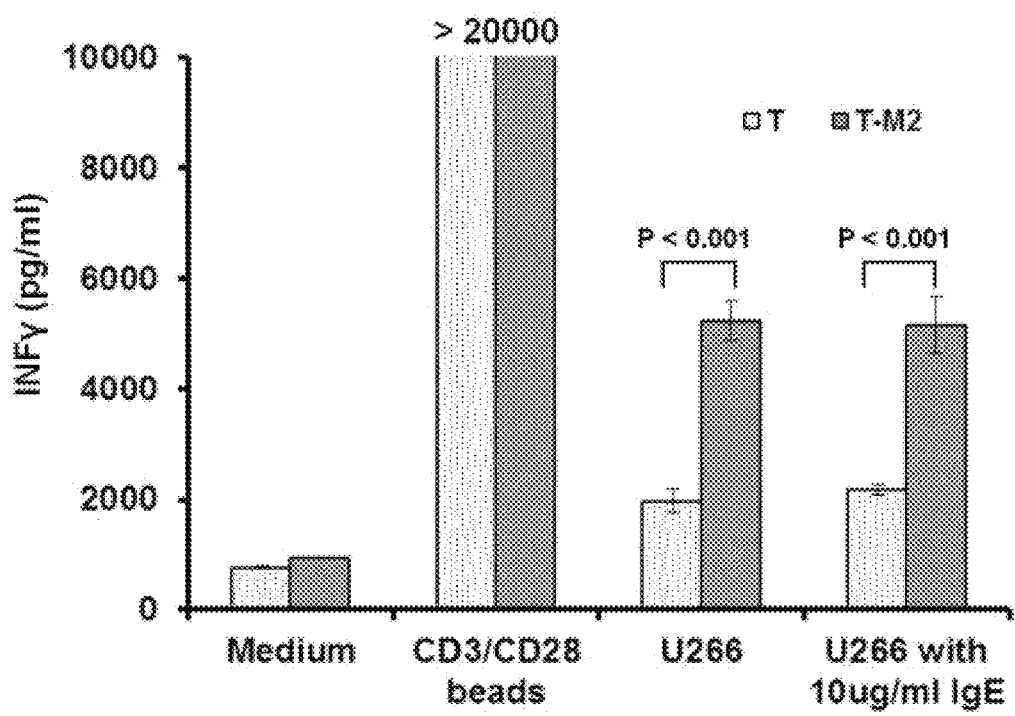
FIG. 5B shows that low affinity FcεRIα-based CAR M2 mediated human CD8+ T cell responses to U266 cells in the presence of free IgE. 0.125×10$^6$ untransduced human CD8+ T cells or human CD8+ T cells transduced with the M2 CAR were stimulated with equal numbers of CD3/CD28 beads, U266 cells, or U266 cells in the presence of 10 μg/ml free IgE. The cells were incubated for 24 hours and the IFNγ concentrations in the supernatant were measured using ELISA. The data points are averaged values of triplicates with error bars representing standard deviation.
Figure 5C:
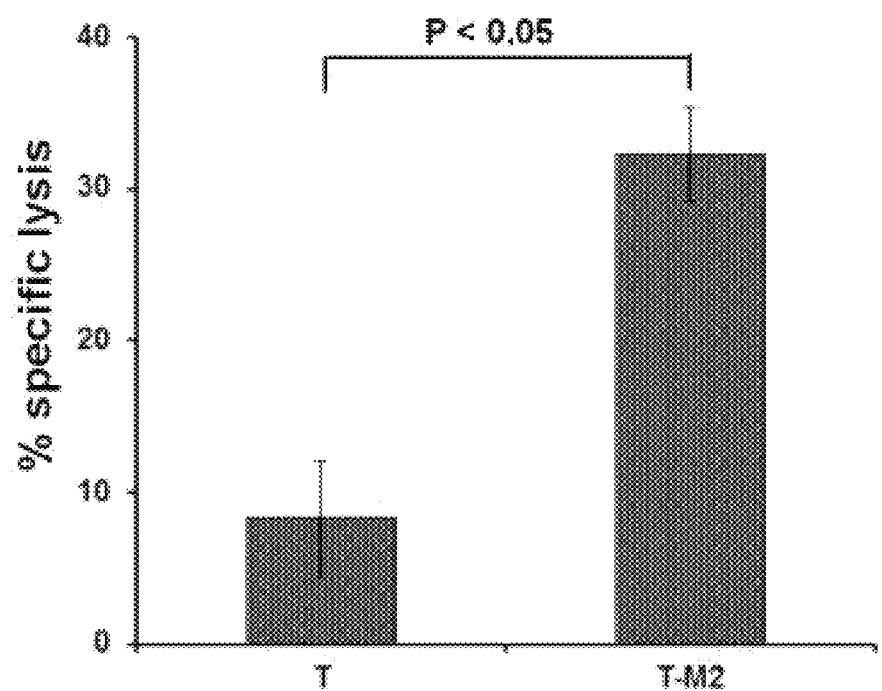
FIG. 5C shows the killing of U266 cells by primary human CD8+ T cells expressing the M2 CAR. U266 cells stably expressing luciferase (U266-luci) were cultured with CD8+ T cells expressing the M2 CAR at an 1:3 ratio and for 20 hours. The percentage of specific lysis was measured based on the luciferase activity in the live U266-luci cells. The data points are averaged values of duplicates with error bars representing standard error.

The low affinity M2 CAR on purified primary human CD8+ T cells was expressed using lentiviral vectors (FIG. 5A). As expected, both control T cells without M2 CAR expression and M2 CAR+ T cells displayed robust INFγ responses to beads coated with anti-CD3 and anti-CD28 antibodies (FIG. 5B). M2 CAR+ cells, however, produced much higher levels of INFγ than control T cells, indicating M2 CAR-mediated specific T cell responses. Consistent with data from Jurkat cells (FIG. 3C), addition of IgE at the concentration of 10 µg/ml did not inhibit T cell responses.

To test the ability of human T cells expressing M2 CARs to kill U266 cells, U266-luci cells that stably express then fire fly luciferase were generated. When the cells are killed, the intracellular luciferase activity is inactivated without leaking into the culture media. Measuring target cells killing based on the luciferase activity of remaining live cells has been shown to outperform standard $^{51}$Cr release assay (Baldwin et al., *PLoS One*. 2014; 9(2):e89357). As shown in FIG. 5C, human CD8+ T cells expressing the M2 CAR showed more than 3-fold killing activity than control cells. Taken together, these results demonstrated that when expressed on primary human CD8+ T cells, the low affinity FcεRI-based M2 CAR mediated robust T cell responses in terms of cytokine production and killing to target cells expressing low levels of mIgE.

The disclosures of each and every patent, patent application, GenBank record, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

I claim:

1. An isolated nucleic acid sequence encoding a chimeric antigen receptor (CAR), wherein the CAR comprises a human FcεRIα extracellular domain, a CD3ζ extracellular domain, a CD3ζ transmembrane domain, and an intracellular signaling domain comprising at least one imunoreceptor tyrosine-based activation motif (ITAM) of a CD3ζ signaling domain.

2. The isolated nucleic acid according to claim 1, further encoding a costimulatory signaling domain disposed between the CD3ζ transmembrane domain and the intracellular signaling domain.

3. The isolated nucleic acid according to claim 2, wherein the encoded costimulatory domain comprises at least the intracellular domain of at least one of 4-1BB, CD27, CD28, CD134 or ICOS.

4. The isolated nucleic acid according to claim 1, wherein the encoded FcεRIαextracellular domain is a mutant FcεRIα extracellular domain that has a reduced binding affinity for human IgE compared to wild type human FcεRIα extracellular domain.

5. The isolated nucleic acid sequence according to claim 4, wherein the encoded mutant human FcεRIα extracellular domain comprises an amino acid sequence wherein at least one amino acid position is substituted with another amino acid compared to wild type human FcεRIα.

6. The isolated nucleic acid sequence according to claim 4, wherein the encoded mutant human FcεRIα extracellular domain comprises the amino acid sequence of SEQ ID NO: 1, wherein at least one amino acid position in SEQ ID NO: 1 is substituted with another amino acid.

7. The isolated nucleic acid sequence according to claim 6, wherein the encoded mutant human FcεRIα extracellular domain comprises the amino acid sequence of SEQ ID NO: 1, wherein from 1 to 6 amino acid positions in SEQ ID NO: 1 are substituted with another amino acid.

8. The isolated nucleic acid sequence according to claim 6, wherein the encoded mutant human FcεRIα extracellular domain comprises the amino acid sequence of SEQ ID NO: 1, wherein at least one of the following amino acid positions is substituted by another amino acid: Trp113, Lys117, Val155 or Asp159.

9. The isolated nucleic acid sequence according to claim 8, wherein the encoded mutant human FcεRIα extracellular domain comprises the amino acid sequence of SEQ ID NO: 1, wherein at least one of the following mutations is present: Trp113Ala, Lys117Asp, Val155Ala or Asp159Ala.

10. The isolated nucleic acid sequence according to claim 9 wherein the encoded mutant human FcεRIα extracellular domain comprises the amino acid sequence of SEQ ID NO: 1, with one of the following single or double mutations being present: Lys117Asp; Lys117Asp and Asp159Ala; Lys117Asp and Trp113Ala; or Lys117Asp and Val155Ala.

11. The isolated nucleic acid sequence according to claim 1, wherein the encoded CD3ζ signaling domain has the amino acid sequence of SEQ ID NO: 5.

12. The isolated nucleic acid sequence according to claim 1, wherein the encoded CD3ζ transmembrane domain has the amino acid sequence of SEQ ID NO: 11.

13. The isolated nucleic acid sequence according to claim 1, wherein the encoded CD3ζ extracellular domain has the amino acid sequence of SEQ ID NO: 33.

14. The isolated nucleic acid sequence according to claim 3, encoding a CAR wherein the costimulatory signaling domain comprises the intracellular domain of CD28 or 4-1BB, or the intracellular domains of both CD28 and 4-1BB.

15. The isolated nucleic acid sequence according to claim 1, wherein the encoded CAR comprises at its N-terminus a human CD3ζ signal peptide.

16. The isolated nucleic acid sequence according to claim 1, comprising a nucleic acid sequence selected from the group consisting of the following:
(a) SEQ ID NO: 28;
(b) the contiguous sequence of nucleotides from nucleotide 76 to nucleotide 1059 of SEQ ID NO: 28;
(c) SEQ ID NO: 20;
(d) the contiguous sequence of nucleotides from nucleotide 76 to nucleotide 1059 of SEQ ID NO: 20;
(e) SEQ ID NO: 22;
(f) the contiguous sequence of nucleotides from nucleotide 76 to nucleotide 1059 of SEQ ID NO: 22;
(g) SEQ ID NO: 24;
(h) the contiguous sequence of nucleotides from nucleotide 76 to nucleotide 1059 of SEQ ID NO: 24;
(i) SEQ ID NO: 26; and
(j) the contiguous sequence of nucleotides from nucleotide 76 to nucleotide 1059 of SEQ ID NO: 26.

17. A chimeric; antigen receptor (CAR) comprising a human FcεRIα extracellular domain, a CD3ζ extracellular domain, a CD3ζ transmembrane domain, and an intracellular signaling domain comprising at least one immunoreceptor tyrosine-based activation motif (ITAM) of a CD3ζ signaling domain.

18. The CAR according to claim 17, further comprising a costimulatory signaling domain disposed between the CD3ζ transmembrane domain and the intracellular signaling domain.

19. The CAR according to claim 18, wherein the costimulatory domain comprises at least the intracellular domain of at least one of 4-1BB, CD27, CD28, CD134 or ICOS.

20. The CAR according to claim 17, wherein the FcεRIα extracellular domain is a mutant FcεRIα extracellular domain that has a reduced binding affinity for human IgE compared to wild type human FcεRIα, extracellular domain.

21. The CAR according to claim 20, wherein the mutant human FcεRIα extracellular domain comprises an amino acid sequence wherein at least one amino acid position is substituted with another amino acid compared to wild type human FcεRIα.

22. The CAR according to claim 20, wherein the encoded mutant human FcεRIα extracellular domain comprises the ammo acid sequence of SEQ NO: 1, wherein at least one amino acid position in SEQ ID NO: 1 is substituted with another amino acid.

23. The CAR according to claim 22, wherein the encoded mutant human FcεRIα extracellular domain comprises the amino acid sequence of SEQ ID NO: 1, wherein from 1 to 6 amino acid positions in SEQ ID NO: 1 is substituted with another amino acid.

24. The CAR according to claim 22, wherein the mutant human FcεRIα extracellular domain comprises the amino acid sequence of SEQ ID NO: 1, wherein at least one of the following amino acid positions is substituted by another amino acid: Trp113, Lys117, Val155 or Asp159.

25. The CAR according to claim 24, wherein the mutant human FcεRIα extracellular domain comprises the amino acid sequence of SEQ ID NO: 1, wherein at least one of the following mutations are present: Trp113Ala, Lys117Asp, Val155Ala or Asp159Ala.

26. The CAR according to claim 25, wherein the mutant human FcεRIα extracellular domain comprises the amino acid sequence of SEQ ID NO: 2, with one of the following single or double mutations being present: Lys117Asp; Lys117Asp and Asp159Ala; Lys117Asp and Trp113Ala; or Lys117Asp and Val155Ala.

27. The CAR according to claim 17, wherein the CD3ζ signaling domain has the amino acid sequence of SEQ ID NO: 5.

28. The CAR according to claim 17, wherein the CD3ζ transmembrane domain has the amino acid sequence of SEQ ID NO: 11.

29. The CAR according to claim 24, wherein the intracellular signaling domain has the amino acid sequence of SEQ ID NO: 33.

30. The CAR according to claim 19, wherein the costimulatory signaling domain comprises the intracellular domain of CD28 or 4-1BB, or the intracellular domain of both CD28 and 4-1BB.

31. The CAR according to claim 17, further comprising at its N-terminus a human CD3ζ signal peptide.

32. The CAR according to claim 17, wherein the CAR comprises an amino acid sequence selected from the group of amino acids consisting of the following:
(a) SEQ ID NO: 27;
(b) the contiguous sequence of amino acids from amino acid 26 to amino acid 353 of SEQ ID NO: 27;
(c) SEQ ID NO: 19;
(d) the contiguous sequence of amino acids from amino acid 26 to amino acid 353 of SEQ ID NO: 19;
(e) SEQ ID NO: 21;
the contiguous sequence of amino acids from amino acid 26 to amino acid 353 of SEQ ID NO: 21;
(g) SEQ ID NO: 23;
(h) the contiguous sequence of amino acids from amino acid 26 to amino acid 353 of SEQ ID NO: 23;
(i) SEQ ID NO: 25; and
(j) the contiguous sequence of amino acids from amino acid 26 to amino acid 353 of SEQ ID NO: 25.

33. A T cell comprising a nucleic acid sequence encoding a chimeric antigen receptor (CAR), the CAR comprising a human FcεRIα extracellular domain, a CD3ζ extracellular domain, a CD3ζ transmembrane domain, and an intracellular signaling domain comprising at least one immunoreceptor tyrosine-based activation motif (ITAM) of a CD3ζ signaling domain.

34. The T-cell according to claim 33, wherein the FcεRIα extracellular domain is a mutant FcεRIα extracellular domain that has a reduced binding affinity for human IgE compared to wild type human FcεRIα extracellular domain.

35. A T cell expressing a chimeric antigen receptor (CAR), the CAR comprising a human FcεRIα extracellular domain, a CD3ζ extracellular domain, a CD3ζ transmembrane domain, and an intracellular signaling domain comprising at least one immunoreceptor tyrosine-based activation motif (ITAM) of a CD3ζ signaling domain.

36. The T cell according to claim 35, wherein the CAR further comprises a costimulatory signaling domain disposed between the CD3ζ transmembrane domain and the intracellular signaling domain.

37. The T cell according to claim 36, wherein the costimulatory domain comprises at least the intracellular domain of at least one of 4-1BB, CD27, CD28, CD134 or ICOS.

38. The T-cell according to claim 35, wherein the FcεRIα extracellular domain is a mutant FcεRIα extracellular domain that has a reduced binding affinity for human IgE compared to wild type human FcεRIα extracellular domain.

39. The T cell according to claim 38, wherein the mutant human FcεRIα extracellular domain comprises an amino acid sequence wherein at least one amino acid position is substituted with another amino acid compared to wild type human FcεRIα.

40. The T cell according to claim 39, wherein the encoded mutant human FcεRIα extracellular domain comprises the amino acid sequence of SEQ ID NO: 1, wherein at least one amino acid position in SEQ ID NO: 1 is substituted with another amino acid.

41. T cell according to claim 40, wherein the encoded mutant human FcεRIα extracellular domain comprises the amino acid sequence of SEQ ID NO: 1, wherein from 1 to 6 amino acid positions in SEQ ID NO: 1 are substituted with another amino acid.

42. The T cell according to claim 40, wherein the mutant human FcεRIα extracellular domain comprises the amino acid sequence of SEQ ID NO: 1, wherein at least one of the following amino acid positions is substituted by another amino acid: Trp113, Lys117, Val155 or Asp159.

43. The T cell according to claim 42, wherein the mutant human FcεRIα extracellular domain comprises the amino acid sequence of SEQ ID NO: 1, wherein at least one of the following mutations is present: Trp113Ala, Lys117Asp, Val155Ala or Asp159A.

44. The T cell according to claim 43, wherein the mutant human FcεRIα extracellular domain comprises the amino acid sequence of SEQ ID NO: 1, with one of the following single or double mutations being present: Lys117Asp; Lys117Asp and Asp159Ala; Lys117Asp and Trp113Ala; or Lys117Asp and Val155Ala.

45. The T cell according to claim 33, wherein the CD3ζ signaling domain has the amino acid sequence of SEQ ID NO: 5.

46. The T cell according to claim 33, wherein the CD3ζ transmembrane domain has the amino acid sequence of SEQ ID NO: 11.

47. The T cell according to claim 33, wherein CD3ζ extracellular domain has the amino acid sequence of SEQ ID NO: 33.

48. The T cell according to claim 37, wherein the costimulatory signaling domain comprises the intracellular domain of CD28 or 4-1BB, or the intracellular domain of both CD28 and 4-1BB.

49. The T cell according to claim 35, wherein the CAR comprises an amino acid sequence selected from the group of amino acids consisting of the following:
  (a) SEQ ID NO: 27;
  (b) the contiguous sequence of amino acids from amino acid 26 to amino acid 353 of SEQ ID NO: 27;
  (c) SEQ ID NO: 19;
  (d) the contiguous sequence of amino acids from amino acid 26 to amino acid 353 Of SEQ ID NO: 19;
  (e) SEQ ID NO: 21;
  the contiguous sequence of amino acids from amino acid 26 to amino acid 353 of SEQ ID NO: 21;
  (g) SEQ ID NO: 23;
  (h) the contiguous sequence of amino acids from amino acid 26 to amino acid 353 of SEQ NO: 23;
  (i) SEQ Id NO: 25; and
  (j) the contiguous sequence of amino acids from amino acid 26 to amino acid 353 of SEQ ID NO: 25.

50. A vector comprising a nucleic acid sequence encoding a chimeric antigen receptor (CAR), the CAR comprising a human FcεRIα extracellular domain, a CD3ζ extracellular domain, a CD3ζ transmembrane domain, and an intracellular signaling domain comprising at least one immuinoreceptor tyrosine-based activation motif (ITAM) of a CD3ζ signaling domain.

51. The vector according to claim 50, wherein the encoded FcεRIα extracellular domain is a mutant FcεRIα extracellular domain that that has a reduced binding affinity for human IgE compared to wild type human FcεRIα extracellular domain.

52. The vector according to claim 51, wherein: the encoded mutant human FcεRIα extracellular domain comprises the amino acid sequence of SEQ ID NO: 1, wherein at least one of the following amino acid positions is substituted by another amino acid: Trp113, Lys117, Val155 or Asp159.

53. The vector according to claim 52, wherein the encoded mutant human FcεRIα extracellular domain comprises the amino acid sequence of SEQ ID NO: 2, wherein at least one of the following mutations is present: Trp113Ala, Lys117Asp, Val155Ala or Asp159Ala.

54. The vector according to claim 53, wherein the encoded mutant human FcεRIα extracellular domain comprises the amino acid sequence of SEQ ID NO: 1, with one of the following single or double mutations being present: Lys117Asp; Lys117Asp and Asp159Ala; Lys117Asp and Trp113Ala; or Lys117Asp and Val155Ala.

55. The vector according to claim 50, wherein the encoded CD3ζ signaling domain has the amino acid sequence of SEQ ID NO: 5.

56. The vector according to claim 50, wherein the encoded CD3ζ transmembrane domain has the amino acid sequence of SEQ ID NO: 11.

57. The vector according to claim 50, wherein the encoded CD3ζ extracellular domain has the amino acid sequence of SEQ ID NO: 33.

58. The vector according to claim 50, encoding a CAR wherein the costimulatory signaling domain comprises the intracellular domain of CD28 or 4-1BB, or the intracellular domains of both CD28 and 4-1BB.

59. The vector according to claim 50, comprising a nucleic acid sequence selected from the group consisting of the following:
  (a) SEQ II) NO: 28;
  (b) the contiguous sequence of nucleotides from nucleotide 76 to nucleotide 1059 of SEQ ID NO: 28;
  (c) SEQ ID NO: 20;
  (d) the contiguous sequence of nucleotides from nucleotide 76 to nucleotide 1059 of SEQ ID NO: 20;
  (e) SEQ ID NO: 22;
  (f) the contiguous sequence of nucleotides from nucleotide 76 to nucleotide 1059 of SEQ ID NO: 22;
  (g) SEQ H) NO: 24;
  (h) the contiguous sequence of nucleotides from nucleotide 76 to nucleotide 1059 of SEQ ID NO: 24;
  (i) SEQ ID NO: 26; and
  (j) the contiguous sequence of nucleotides from nucleotide 76 to nucleotide 1059 of SEQ ID NO: 26.

60. A method for stimulating a T cell-mediated immune response to IgE-producing cells expressing the transmembrane form of human IgE (mIgE) in a subject, the method comprising administering to the subject an effective amount of a T cell expressing a chimeric antigen receptor (CAR) that directly binds to the transmembrane form of human IgE (mIgE), wherein the CAR comprises a human FcεRIα extracellular domain, a transmembrane domain, and an intracellular signaling domain comprising at least one immunoreceptor tyrosine-based activation motif ITAM).

61. The method according to claim 60, wherein the T cells comprise autologous T cells that are removed from the subject and engineered ex vivo to express said CAR and administered to the subject.

62. A method for treating an IgE-mediated allergic disease in a subject in need of such treatment, or for preventing an IgE-mediated allergic disease in a subject at risk of such disease, comprising administering to the subject an effective amount of a T cell expressing a chimeric, antigen receptor (CAR) that directly binds to the transmembrane form of human IgE(mIgE) on the surface of IgE-producing cells, wherein the CAR comprises a human Fcεα extracellular domain, a transmembrane domain, and an intracellular signaling domain comprising at least one immunoreceptor tyrosine-based activation mold (ITAM).

63. The method according to claim 62, wherein the T cells comprise autologous T cells that are removed from the subject and engineered ex vivo to express said CAR and administered to the subject.

64. The method according to claim 63, wherein the disease is selected from the group consisting of allergic asthma, food allergy, atopic dermatitis, allergic rhinitis, allergic rhinoconjunctivitis, chronic urticaria and systematic anaphylaxis.

65. The method according to claim 60, wherein the CAR mediates T-cell activation and cytotoxicity towards IgE-producing cells.

66. The method according to claim 60, wherein the human FcεRIα extracellular domain is wild type or mutated.

67. The method according to claim 66, wherein the mutant human FcεRIα extracellular domain has a reduced binding affinity for human IgE, compared to wild type human FcεRIα extracellular domain.

68. The method according to claim 66, wherein the mutant human FcεRIα extracellular domain comprises an amino acid sequence wherein at least one amino acid position is substituted with another amino acid compared to wild type human FcεRIα.

69. The method according to claim 66, wherein the mutant human FcεRIα extracellular domain comprises the amino acid sequence of SEQ ID NO: 1, wherein at least one of the following amino acid positions is substituted by another amino acid: Trp113, Lys117, Val155 or Asp159.

70. The method according to claim 60, wherein the intracellular signaling domain comprises at least one of 4-1BB, CD27, CD28, CD134, or ICOS.

71. The method according to claim 62, wherein the CAR mediates T cell activation and cytotoxicity towards IgE-producing cells.

72. The method according to claim 62, wherein the human FcεRIα extracellular domain is wild type or mutated.

73. The method according to claim 72, wherein the mutant human FcεRIα extracellular domain has a reduced binding affinity for human IgE compared to wild type human FcεRIα extracellular domain.

74. The method according to claim 72, wherein the mutant human FcεRIα extracellular domain comprises an amino acid sequence wherein at least one amino acid position is substituted with another amino acid compared to wild type human FcεRIα.

75. The method according to claim 72, wherein the mutant human FcεRIα extracellular domain comprises the amino acid sequence of SEQ ID NO: 1, wherein at least one of the following amino acid positions is substituted by another amino acid: Trp113, Lys117, Val155 or Asp159.

76. The method according to claim 62, wherein the CAR is arranged, wherein the intracellular signaling domain comprises at least one of 4-1BB, CD27, CD28, CD134, or ICOS.

77. The isolated nucleic acid according to claim 1, wherein the CAR is arranged, from N-terminus to C-terminus, as the human FcεRIα extracellular domain, the CD3ζ extracellular domain, the CD3ζ transmembrane domain, and the intracellular signaling domain.

78. The CAR according to claim 17, wherein the CAR is arranged, from N-terminus to C-terminus, as the human FcεRIα extracellular domain, the CD3ζ extracellular domain, the CD3ζ transmembrane domain, and the intracellular signaling domain.

79. The T cell according to claim 33, wherein the CAR is arranged, from N-terminus to C-terminus, as the human FcεRIα extracellular domain, the CD3ζ extracellular domain, the CD3ζ transmembrane domain, and the intracellular signaling domain.

80. The T cell according to claim 35, wherein the CAR is arranged, from N-terminus to C-terminus, as the human FcεRIα extracellular domain, the CD3ζ extracellular domain, the CD3ζ transmembrane domain, and the intracellular signaling domain.

81. The vector according to claim 50, wherein the CAR is arranged, from N-terminus to C-terminus, as the human FcεRIα extracellular domain, the CD3ζ extracellular domain, the CD3ζ transmembrane domain, and the intracellular signaling domain.

* * * * *

SEQUENCE LISTING

<160> NUMBER OF SEQ ID NOS: 37

<210> SEQ ID NO 1
<211> LENGTH: 180
<212> TYPE: PRT
<213> ORGANISM: Homo sapiens

<400> SEQUENCE: 1

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln
            180

<210> SEQ ID NO 2
<211> LENGTH: 540
<212> TYPE: DNA
<213> ORGANISM: Homo sapiens

<400> SEQUENCE: 2
gtccctcaga aacctaaggt ctccttgaac cctccatgga atagaatatt taaaggagag      60
aatgtgactc ttacatgtaa tgggaacaat ttctttgaag tcagttccac caaatggttc     120
cacaatggca gcctttcaga agagacaaat tcaagtttga atattgtgaa tgccaaattt     180
gaagacagtg agaatacaa atgtcagcac caacaagtta tgagagtga acctgtgtac      240 ctggaagtct tcagtgactg gctgctcctt caggcctctg ctgaggtggt gatggagggc     300
cagcccctct tcctcaggtg ccatggttgg aggaactggg atgtgtacaa ggtgatctat     360
tataaggatg gtgaagctct caagtactgg tatgagaacc acaacatctc cattacaaat     420
gccacagttg aagacagtgg aacctactac tgtacgggca agtgtggca gctggactat      480 gagtctgagc ccctcaacat tactgtaata aaagctccgc gtgagaagta ctggctacaa     540

<210> SEQ ID NO 3
<211> LENGTH: 5
<212> TYPE: PRT
<213> ORGANISM: Artificial Sequence
<220> FEATURE:
<223> OTHER INFORMATION: Synthesized linker -continued

<400> SEQUENCE: 3

Gly Gly Ser Gly Gly
1               5

<210> SEQ ID NO 4
<211> LENGTH: 15
<212> TYPE: DNA
<213> ORGANISM: Artificial Sequence
<220> FEATURE:
<223> OTHER INFORMATION: Synthesized linker

<400> SEQUENCE: 4
ggtggatcag gagga                                               15

<210> SEQ ID NO 5
<211> LENGTH: 113
<212> TYPE: PRT
<213> ORGANISM: Homo sapiens

<400> SEQUENCE: 5

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 6
<211> LENGTH: 339
<212> TYPE: DNA
<213> ORGANISM: Homo sapiens

<400> SEQUENCE: 6
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgcag agaaggaaga accctcagga aggcctgtac   180
aatgaactgc agaaagataa gatggcggag gcctacagtg agattgggat gaaaggcgag   240
cgccggaggg gcaaggggca cgatggcctt taccagggtc tcagtacagc caccaaggac   300
acctacgacg cccttcacat gcaggccctg ccccctcgc                          339

<210> SEQ ID NO 7
<211> LENGTH: 25
<212> TYPE: PRT
<213> ORGANISM: Homo sapiens

<400> SEQUENCE: 7

Met Ala Pro Ala Met Glu Ser Pro Thr Leu Leu Cys Val Ala Leu Leu
1               5                   10                  15

Phe Phe Ala Pro Asp Gly Val Leu Ala
            20                  25

<210> SEQ ID NO 8
<211> LENGTH: 75
<212> TYPE: DNA
<213> ORGANISM: Homo sapiens

<400> SEQUENCE: 8
atggctcctg ccatggaatc ccctactcta ctgtgtgtag ccttactgtt cttcgctcca     60
gatggcgtgt tagca                                                     75

<210> SEQ ID NO 9
<211> LENGTH: 9
<212> TYPE: PRT
<213> ORGANISM: Homo sapiens

<400> SEQUENCE: 9

Gln Ser Phe Gly Leu Leu Asp Pro Lys
1               5

<210> SEQ ID NO 10
<211> LENGTH: 27
<212> TYPE: DNA
<213> ORGANISM: Homo sapiens

<400> SEQUENCE: 10
cagagctttg gcctgctgga tcccaaa                                        27

<210> SEQ ID NO 11
<211> LENGTH: 21
<212> TYPE: PRT
<213> ORGANISM: Homo sapiens

<400> SEQUENCE: 11

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 12
<211> LENGTH: 63
<212> TYPE: DNA
<213> ORGANISM: Homo sapiens

<400> SEQUENCE: 12
ctctgctacc tgctggatgg aatcctcttc atctatggtg tcattctcac tgccttgttc     60
ctg                                                                  63

<210> SEQ ID NO 13
<211> LENGTH: 143
<212> TYPE: PRT
<213> ORGANISM: Homo sapiens

<400> SEQUENCE: 13

Gln Ser Phe Gly Leu Leu Asp Pro Lys Leu Cys Tyr Leu Leu Asp Gly
1               5                   10                  15

Ile Leu Phe Ile Tyr Gly Val Ile Leu Thr Ala Leu Phe Leu Arg Val
            20                  25                  30

Lys Phe Ser Arg Ser Ala Asp Ala Pro Ala Tyr Gln Gln Gly Gln Asn
        35                  40                  45

Gln Leu Tyr Asn Glu Leu Asn Leu Gly Arg Arg Glu Glu Tyr Asp Val
    50                  55                  60

Leu Asp Lys Arg Arg Gly Arg Asp Pro Glu Met Gly Gly Lys Pro Gln
65                  70                  75                  80

Arg Arg Lys Asn Pro Gln Glu Gly Leu Tyr Asn Glu Leu Gln Lys Asp
                85                  90                  95

Lys Met Ala Glu Ala Tyr Ser Glu Ile Gly Met Lys Gly Glu Arg Arg
            100                 105                 110

Arg Gly Lys Gly His Asp Gly Leu Tyr Gln Gly Leu Ser Thr Ala Thr
        115                 120                 125

Lys Asp Thr Tyr Asp Ala Leu His Met Gln Ala Leu Pro Pro Arg
    130                 135                 140

<210> SEQ ID NO 14
<211> LENGTH: 429
<212> TYPE: DNA
<213> ORGANISM: Homo sapiens

<400> SEQUENCE: 14
cagagctttg gcctgctgga tcccaaactc tgctacctgc tggatggaat cctcttcatc     60
tatggtgtca ttctcactgc cttgttcctg agagtgaagt tcagcaggag cgcagacgcc    120
cccgcgtacc agcagggcca gaaccagctc tataacgagc tcaatctagg acgaagagag    180
gagtacgatg ttttggacaa gagacgtggc cgggaccctg agatgggggg aaagccgcag    240
agaaggaaga accctcagga aggcctgtac aatgaactgc agaaagataa gatggcggag    300
gcctacagtg agattgggat gaaaggcgag cgccggaggg gcaaggggca cgatggcctt    360
taccagggtc tcagtacagc caccaaggac acctacgacg cccttcacat gcaggccctg    420
ccccctcgc                                                            429

<210> SEQ ID NO 15
<211> LENGTH: 42
<212> TYPE: PRT
<213> ORGANISM: Homo sapiens

<400> SEQUENCE: 15

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 16
<211> LENGTH: 126
<212> TYPE: DNA
<213> ORGANISM: Homo sapiens

<400> SEQUENCE: 16
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                               126

<210> SEQ ID NO 17
<211> LENGTH: 41
<212> TYPE: PRT
<213> ORGANISM: Homo sapiens

```
<400> SEQUENCE: 17

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 18
<211> LENGTH: 123
<212> TYPE: DNA
<213> ORGANISM: Homo sapiens

<400> SEQUENCE: 18
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                  123

<210> SEQ ID NO 19
<211> LENGTH: 353
<212> TYPE: PRT
<213> ORGANISM: Artificial Sequence
<220> FEATURE:
<223> OTHER INFORMATION: Synthesized, comprising: CD3-zeta signal
      peptide; Fc-epsilon-RI-alpha' extracellular domain (mutated);
      spacer; and CD3-zeta extracellular, transmembrane and signaling
      domains.

<400> SEQUENCE: 19

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Asp Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Gly Gly Ser
        195                 200                 205

Gly Gly Gln Ser Phe Gly Leu Leu Asp Pro Lys Leu Cys Tyr Leu Leu
```

```
Asp Gly Ile Leu Phe Ile Tyr Gly Val Ile Leu Thr Ala Leu Phe Leu
225                 230                 235                 240

Arg Val Lys Phe Ser Arg Ser Ala Asp Ala Pro Ala Tyr Gln Gln Gly
                245                 250                 255

Gln Asn Gln Leu Tyr Asn Glu Leu Asn Leu Gly Arg Arg Glu Glu Tyr
            260                 265                 270

Asp Val Leu Asp Lys Arg Arg Gly Arg Asp Pro Glu Met Gly Gly Lys
        275                 280                 285

Pro Gln Arg Arg Lys Asn Pro Gln Glu Gly Leu Tyr Asn Glu Leu Gln
    290                 295                 300

Lys Asp Lys Met Ala Glu Ala Tyr Ser Glu Ile Gly Met Lys Gly Glu
305                 310                 315                 320

Arg Arg Arg Gly Lys Gly His Asp Gly Leu Tyr Gln Gly Leu Ser Thr
                325                 330                 335

Ala Thr Lys Asp Thr Tyr Asp Ala Leu His Met Gln Ala Leu Pro Pro
            340                 345                 350

Arg
```

<210> SEQ ID NO 20
<211> LENGTH: 1059
<212> TYPE: DNA
<213> ORGANISM: Homo sapiens

<400> SEQUENCE: 20

```
atggctcctg ccatggaatc ccctactcta ctgtgtgtag ccttactgtt cttcgctcca    60
gatggcgtgt tagcagtccc tcagaaacct aaggtctcct tgaaccctcc atggaataga   120
atatttaaag agagaatgtg actcttaca gtgtaatggga acaatttctt tgaagtcagt    180
tccaccaaat ggttccacaa tggcagcctt tcagaagaga caaattcaag tttgaatatt    240
gtgaatgcca aatttgaaga cagtggagaa tacaaatgtc agcaccaaca agttaatgag    300
agtgaacctg tgtacctgga agtcttcagt gactggctgc tccttcaggc ctctgctgag    360
gtggtgatgg agggccagcc cctcttcctc aggtgccatg gttggaggaa ctgggatgtg    420
tacgatgtga tctattataa ggatggtgaa gctctcaagt actggtatga gaaccacaac    480
atctccatta caaatgccac agttgaagac agtggaacct actactgtac gggcaaagtg    540
tggcagctgg actatgagtc tgagcccctc aacattactg taataaaagc tccgcgtgag    600
aagtactggc tacaaggtgg atcaggagga cagagctttg gcctgctgga tcccaaactc    660
tgctacctgc tggatggaat cctcttcatc tatggtgtca ttctcactgc cttgttcctg    720
agagtgaagt tcagcaggag cgcagacgcc cccgcgtacc agcagggcca gaaccagctc    780
tataacgagc tcaatctagg acgaagagag gagtacgatg ttttggacaa gagacgtggc    840
cgggaccctg agatgggggg aaagccgcag agaaggaaga accctcagga aggcctgtac    900
aatgaactga gaaagataaa gatggcggag gcctacagtg agattgggat gaaaggcgag    960
cgccggaggg gcaaggggca cgatggcctt taccagggtc tcagtacagc caccaaggac   1020
acctacgacg cccttcacat gcaggccctg cccctcgc                          1059
```

<210> SEQ ID NO 21
<211> LENGTH: 353
<212> TYPE: PRT
<213> ORGANISM: Homo sapiens

<400> SEQUENCE: 21

```
Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Asp Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Ala Tyr Glu Ser Glu Pro Leu Asn Ile
            180                 185                 190

Thr Val Ile Lys Ala Pro Arg Glu Lys Tyr Trp Leu Gln Gly Gly Ser
        195                 200                 205

Gly Gly Gln Ser Phe Gly Leu Leu Asp Pro Lys Leu Cys Tyr Leu Leu
    210                 215                 220

Asp Gly Ile Leu Phe Ile Tyr Gly Val Ile Leu Thr Ala Leu Phe Leu
225                 230                 235                 240

Arg Val Lys Phe Ser Arg Ser Ala Asp Ala Pro Ala Tyr Gln Gln Gly
                245                 250                 255

Gln Asn Gln Leu Tyr Asn Glu Leu Asn Leu Gly Arg Arg Glu Glu Tyr
            260                 265                 270

Asp Val Leu Asp Lys Arg Arg Gly Arg Asp Pro Glu Met Gly Gly Lys
        275                 280                 285

Pro Gln Arg Arg Lys Asn Pro Gln Glu Gly Leu Tyr Asn Glu Leu Gln
    290                 295                 300

Lys Asp Lys Met Ala Glu Ala Tyr Ser Glu Ile Gly Met Lys Gly Glu
305                 310                 315                 320

Arg Arg Arg Gly Lys Gly His Asp Gly Leu Tyr Gln Gly Leu Ser Thr
                325                 330                 335

Ala Thr Lys Asp Thr Tyr Asp Ala Leu His Met Gln Ala Leu Pro Pro
            340                 345                 350

Arg

<210> SEQ ID NO 22
<211> LENGTH: 1059
<212> TYPE: DNA
<213> ORGANISM: Artificial Sequence
<220> FEATURE:
<223> OTHER INFORMATION: Synthesized, encoding: CD3-zeta signal
      peptide; Fc-epsilon-RI-alpha' extracellular domain (mutated);
      spacer; and CD3-zeta extracellular, transmembrane and signaling
      domains.
```

<400> SEQUENCE: 22

```
atggctcctg ccatggaatc ccctactcta ctgtgtgtag ccttactgtt cttcgctcca        60
gatggcgtgt tagcagtccc tcagaaacct aaggtctcct tgaaccctcc atggaataga       120
atatttaaag agagaatgt gactcttaca tgtaatggga acaatttctt tgaagtcagt        180
tccaccaaat ggttccacaa tggcagcctt tcagaagaga caaattcaag tttgaatatt       240
gtgaatgcca aatttgaaga cagtggagaa tacaaatgtc agcaccaaca agttaatgag       300
agtgaacctg tgtacctgga agtcttcagt gactggctgc tccttcaggc tctgctgag        360
gtggtgatgg agggccagcc cctcttcctc aggtgccatg gttggaggaa ctgggatgtg       420
tacgatgtga tctattataa ggatggtgaa gctctcaagt actggtatga accacaac        480
atctccatta caaatgccac agttaagac agtggaacct actactgtac gggcaaagtg       540
tggcagctgg catatgagtc tgagcccctc aacattactg taataaaagc tccgcgtgag       600
aagtactggc tacaaggtgg atcaggagga cagagctttg cctgctgga tcccaaactc        660
tgctacctgc tggatggaat cctcttcatc tatggtgtca ttctcactgc cttgttcctg       720
agagtgaagt tcagcaggag cgcagacgcc ccgcgtacc agcagggcca gaaccagctc        780
tataacgagc tcaatctagg acgaagagag gagtacgatg tttggacaa gagacgtggc        840
cgggaccctg agatgggggg aaagccgcag agaaggaaga accctcagga aggcctgtac       900
aatgaactgc agaaagataa gatggcggag cctacagtg agattgggat gaaaggcgag       960
cgccggaggg gcaagggca cgatggcctt taccagggtc tcagtacagc caccaaggac       1020
acctacgacg cccttcacat gcaggccctg cccctcgc                              1059
```

<210> SEQ ID NO 23
<211> LENGTH: 353
<212> TYPE: PRT
<213> ORGANISM: Artificial Sequence
<220> FEATURE:
<223> OTHER INFORMATION: Synthesized, comprising: CD3-zeta signal
peptide; Fc-epsilon-RI-alpha' extracellular domain (mutated);
spacer; and CD3-zeta extracellular, transmembrane and signaling
domains.

<400> SEQUENCE: 23

```
Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Ala Asp Val Tyr Asp Val Ile
    130                 135                 140
```

Tyr Tyr Lys Asp Gly Glu Ala Leu Lys Tyr Trp Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Gly Gly Ser
        195                 200                 205

Gly Gly Gln Ser Phe Gly Leu Leu Asp Pro Lys Leu Cys Tyr Leu Leu
    210                 215                 220

Asp Gly Ile Leu Phe Ile Tyr Gly Val Ile Leu Thr Ala Leu Phe Leu
225                 230                 235                 240

Arg Val Lys Phe Ser Arg Ser Ala Asp Ala Pro Ala Tyr Gln Gln Gly
                245                 250                 255

Gln Asn Gln Leu Tyr Asn Glu Leu Asn Leu Gly Arg Arg Glu Glu Tyr
            260                 265                 270

Asp Val Leu Asp Lys Arg Arg Gly Arg Asp Pro Glu Met Gly Gly Lys
        275                 280                 285

Pro Gln Arg Arg Lys Asn Pro Gln Glu Gly Leu Tyr Asn Glu Leu Gln
    290                 295                 300

Lys Asp Lys Met Ala Glu Ala Tyr Ser Glu Ile Gly Met Lys Gly Glu
305                 310                 315                 320

Arg Arg Arg Gly Lys Gly His Asp Gly Leu Tyr Gln Gly Leu Ser Thr
                325                 330                 335

Ala Thr Lys Asp Thr Tyr Asp Ala Leu His Met Gln Ala Leu Pro Pro
            340                 345                 350

Arg

<210> SEQ ID NO 24
<211> LENGTH: 1059
<212> TYPE: DNA
<213> ORGANISM: Artificial Sequence
<220> FEATURE:
<223> OTHER INFORMATION: Synthesized, encoding: CD3-zeta signal peptide;
      Fc-epsilon-RI-alpha' extracellular domain (mutated); spacer; and
      CD3-zeta extracellular, transmembrane and signaling domains.

<400> SEQUENCE: 24

```
atggctcctg ccatggaatc ccctactcta ctgtgtgtag ccttactgtt cttcgctcca      60
gatggcgtgt tagcagtccc tcagaaacct aaggtctcct tgaaccctcc atggaataga     120
atatttaaag agagaatgtg actcttaca tgtaatggga acaatttctt tgaagtcagt     180
tccaccaaat ggttccacaa tggcagcctt tcagaagaga caaattcaag tttgaatatt     240
gtgaatgcca aatttgaaga cagtggagaa tacaaatgtc agcaccaaca agttaatgag     300
agtgaacctg tgtacctgga agtcttcagt gactggctgc tccttcaggc tctgctgag     360 gtggtgatgg agggccagcc cctcttcctc aggtgccatg gttggaggaa cgcagatgtg     420
tacgatgtga tctattataa ggatggtgaa gctctcaagt actggtatga gaaccacaac     480
atctccatta caaatgccac agttgaagac agtggaacct actactgtac gggcaaagtg     540
tggcagctgg actatgagtc tgagcccctc aacattacta ataaaagc tccgcgtgag     600 aagtactggc tacaaggtgg atcaggagga cagagctttg gcctgctgga tcccaaactc     660
tgctacctgc tggatggaat cctcttcatc tatggtgtca ttctcactgc cttgttcctg     720
agagtgaagt tcagcaggag cgcagacgcc ccgcgtacc agcagggcca gaaccagctc     780
```

```
tataacgagc tcaatctagg acgaagagag gagtacgatg ttttggacaa gagacgtggc    840
cgggaccctg agatggggg aaagccgcag agaaggaaga accctcagga aggcctgtac    900
aatgaactgc agaaagataa gatggcggag gcctacagtg agattgggat gaaaggcgag    960
cgccggaggg gcaaggggca cgatggcctt taccagggtc tcagtacagc caccaaggac   1020
acctacgacg cccttcacat gcaggccctg ccccctcgc                          1059
```

<210> SEQ ID NO 25
<211> LENGTH: 353
<212> TYPE: PRT
<213> ORGANISM: Artificial Sequence
<220> FEATURE:
<223> OTHER INFORMATION: Synthesized, comprising: CD3-zeta signal
      peptide; Fc-epsilon-RI-alpha' extracellular domain (mutated);
      spacer; and CD3-zeta extracellular, transmembrane and signaling
      domains.

<400> SEQUENCE: 25

```
Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Gly Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Asp Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Ala Trp Gln Leu Asp Tyr Glu Ser Glu Pro Leu Asn Ile
            180                 185                 190

Thr Val Ile Lys Ala Pro Arg Glu Lys Tyr Trp Leu Gln Gly Gly Ser
        195                 200                 205

Gly Gly Gln Ser Phe Gly Leu Leu Asp Pro Lys Leu Cys Tyr Leu Leu
    210                 215                 220

Asp Gly Ile Leu Phe Ile Tyr Gly Val Ile Leu Thr Ala Leu Phe Leu
225                 230                 235                 240

Arg Val Lys Phe Ser Arg Ser Ala Asp Ala Pro Ala Tyr Gln Gln Gly
                245                 250                 255

Gln Asn Gln Leu Tyr Asn Glu Leu Asn Leu Gly Arg Arg Glu Glu Tyr
            260                 265                 270

Asp Val Leu Asp Lys Arg Arg Gly Arg Asp Pro Glu Met Gly Gly Lys
        275                 280                 285

Pro Gln Arg Arg Lys Asn Pro Gln Glu Gly Leu Tyr Asn Glu Leu Gln
    290                 295                 300
```

Lys Asp Lys Met Ala Glu Ala Tyr Ser Glu Ile Gly Met Lys Gly Glu
305                 310                 315                 320

Arg Arg Arg Gly Lys Gly His Asp Gly Leu Tyr Gln Gly Leu Ser Thr
            325                 330                 335

Ala Thr Lys Asp Thr Tyr Asp Ala Leu His Met Gln Ala Leu Pro Pro
            340                 345                 350

Arg

<210> SEQ ID NO 26
<211> LENGTH: 1059
<212> TYPE: DNA
<213> ORGANISM: Artificial Sequence
<220> FEATURE:
<223> OTHER INFORMATION: Synthesized, encoding: CD3-zeta signal peptide;
      Fc-epsilon-RI-alpha' extracellular domain (mutated); spacer; and
      CD3-zeta extracellular, transmembrane and signaling domains.

<400> SEQUENCE: 26
atggctcctg ccatggaatc ccctactcta ctgtgtgtag ccttactgtt cttcgctcca      60
gatggcgtgt tagcagtccc tcagaaacct aaggtctcct tgaaccctcc atggaataga     120
atatttaaag agagaatgt gactcttaca tgtaatggga caatttctt gaagtcagt       180 tccaccaaat ggttccacaa tggcagcctt tcagaagaga caaattcaag tttgaatatt     240
gtgaatgcca aatttgaaga cagtggagaa tacaaatgtc agcaccaaca gttaatgag     300 agtgaacctg tgtacctgga agtcttcagt gactggctgc tccttcaggc ctctgctgag     360
gtggtgatgg agggccagcc cctcttcctc aggtgccatg gttggaggaa ctgggatgtg     420
tacgatgtga tctattataa ggatggtgaa gctctcaagt actggtatga gaaccacaac     480
atctccatta caaatgccac agttgaagac agtggaacct actactgtac gggcaaagca     540
tggcagctgg actatgagtc tgagcccctc aacattactg taataaaagc tccgcgtgag     600
aagtactggc tacaaggtgg atcaggagga cagagctttg gcctgctgga tcccaaactc     660
tgctacctgc tggatggaat cctcttcatc tatggtgtca ttctcactgc cttgttcctg     720
agagtgaagt tcagcaggag cgcagacgcc ccgcgtacc agcagggcca gaaccagctc     780
tataacgagc tcaatctagg acgaagagag gagtacgatg ttttggacaa gagacgtggc     840
cgggaccctg agatgggggg aaagccgcag agaaggaaga accctcagga aggcctgtac     900
aatgaactgc agaaagataa gatggcggag gcctacagtg agattgggat gaaaggcgag     960
cgccggaggg gcaaggggca cgatggcctt taccagggtc tcagtacagc caccaaggac    1020
acctacgacg cccttcacat gcaggccctg ccccctcgc                           1059

<210> SEQ ID NO 27
<211> LENGTH: 353
<212> TYPE: PRT
<213> ORGANISM: Artificial Sequence
<220> FEATURE:
<223> OTHER INFORMATION: Synthesized, comprising: CD3-zeta signal
      peptide; Fc-epsilon-RI-alpha' extracellular domain; spacer; and
      CD3-zeta extracellular, transmembrane and signaling domains.

<400> SEQUENCE: 27

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr 35                  40                  45
Leu Thr Cys Asn Gly Asn Asn Phe Phe Glu Val Ser Ser Thr Lys Trp
 50                  55                  60
Phe His Asn Gly Ser Leu Ser Glu Glu Thr Asn Ser Ser Leu Asn Ile
 65                  70                  75                  80
Val Asn Ala Lys Phe Glu Asp Ser Gly Glu Tyr Lys Cys Gln His Gln
                 85                  90                  95
Gln Val Asn Glu Ser Glu Pro Val Tyr Leu Glu Val Phe Ser Asp Trp
                100                 105                 110
Leu Leu Leu Gln Ala Ser Ala Glu Val Val Met Glu Gly Gln Pro Leu
            115                 120                 125
Phe Leu Arg Cys His Gly Trp Arg Asn Trp Asp Val Tyr Lys Val Ile
130                 135                 140
Tyr Tyr Lys Asp Gly Glu Ala Leu Lys Tyr Trp Tyr Glu Asn His Asn
145                 150                 155                 160
Ile Ser Ile Thr Asn Ala Thr Val Glu Asp Ser Gly Thr Tyr Tyr Cys
                165                 170                 175
Thr Gly Lys Val Trp Gln Leu Asp Tyr Glu Ser Glu Pro Leu Asn Ile
            180                 185                 190
Thr Val Ile Lys Ala Pro Arg Glu Lys Tyr Trp Leu Gln Gly Gly Ser
        195                 200                 205
Gly Gly Gln Ser Phe Gly Leu Leu Asp Pro Lys Leu Cys Tyr Leu Leu
210                 215                 220
Asp Gly Ile Leu Phe Ile Tyr Gly Val Ile Leu Thr Ala Leu Phe Leu
225                 230                 235                 240
Arg Val Lys Phe Ser Arg Ser Ala Asp Ala Pro Ala Tyr Gln Gln Gly
                245                 250                 255
Gln Asn Gln Leu Tyr Asn Glu Leu Asn Leu Gly Arg Arg Glu Glu Tyr
            260                 265                 270
Asp Val Leu Asp Lys Arg Arg Gly Arg Asp Pro Glu Met Gly Gly Lys
        275                 280                 285
Pro Gln Arg Arg Lys Asn Pro Gln Glu Gly Leu Tyr Asn Glu Leu Gln
290                 295                 300
Lys Asp Lys Met Ala Glu Ala Tyr Ser Glu Ile Gly Met Lys Gly Glu
305                 310                 315                 320
Arg Arg Arg Gly Lys Gly His Asp Gly Leu Tyr Gln Gly Leu Ser Thr
                325                 330                 335
Ala Thr Lys Asp Thr Tyr Asp Ala Leu His Met Gln Ala Leu Pro Pro
            340                 345                 350
Arg

<210> SEQ ID NO 28
<211> LENGTH: 1059
<212> TYPE: DNA
<213> ORGANISM: Artificial Sequence
<220> FEATURE:
<223> OTHER INFORMATION: Synthesized, encoding: CD3-zeta signal peptide;
    Fc-epsilon-RI-alpha' extracellular domain; spacer; and CD3-zeta
    extracellular, transmembrane and signaling domains.

<400> SEQUENCE: 28
atggctcctg ccatggaatc ccctactcta ctgtgtgtag ccttactgtt cttcgctcca      60
gatggcgtgt tagcagtccc tcagaaacct aaggtctcct tgaaccctcc atggaataga    120
atatttaaag gagagaatgt gactcttaca tgtaatggga caaatttctt tgaagtcagt    180

```
tccaccaaat ggttccacaa tggcagcctt tcagaagaga caaattcaag tttgaatatt      240
gtgaatgcca aatttgaaga cagtggagaa tacaaatgtc agcaccaaca agttaatgag      300
agtgaacctg tgtacctgga agtcttcagt gactggctgc tccttcaggc ctctgctgag      360
gtggtgatgg agggccagcc cctcttcctc aggtgccatg gttggaggaa ctgggatgtg      420
tacaaggtga tctattataa ggatggtgaa gctctcaagt actggtatga gaaccacaac      480
atctccatta caaatgccac agttgaagac agtggaacct actactgtac gggcaaagtg      540
tggcagctgg actatgagtc tgagcccctc aacattactg taataaaagc tccgcgtgag      600
aagtactggc tacaaggtgg atcaggagga cagagctttg cctgctgga tcccaaactc       660 tgctacctgc tggatggaat cctcttcatc tatggtgtca ttctcactgc cttgttcctg      720
agagtgaagt tcagcaggag cgcagacgcc ccgcgtacc agcagggcca gaaccagctc       780
tataacgagc tcaatctagg acgaagagag gagtacgatg ttttggacaa gagacgtggc      840
cgggaccctg agatgggggg aaagccgcag agaaggaaga accctcagga aggcctgtac      900
aatgaactgc agaaagataa gatggcgagg cctacagtg agattgggat gaaaggcgag       960
cgccggaggg gcaaggggca cgatggcctt taccagggtc tcagtacagc caccaaggac     1020
acctacgacg cccttcacat gcaggccctg cccctcgc                             1059
```

<210> SEQ ID NO 29
<211> LENGTH: 38
<212> TYPE: DNA
<213> ORGANISM: Artificial Sequence
<220> FEATURE:
<223> OTHER INFORMATION: Synthesized. Forward primer for obtaining
      truncated cDNA encoding the two extracellular domains of human
      Fc-epsilon-RI-alpha

<400> SEQUENCE: 29
gcgcgcaagc ttcgccgcca ccatggctcc tgccatgg                                38

<210> SEQ ID NO 30
<211> LENGTH: 32
<212> TYPE: DNA
<213> ORGANISM: Artificial Sequence
<220> FEATURE:
<223> OTHER INFORMATION: Synthesized. Reverse primer for obtaining
      truncated cDNA encoding the two extracellular domains of human
      Fc-epsilon-RI-alpha

<400> SEQUENCE: 30
gcgcgcgaat tcatcacttc tcacgcggag ct                                      32

<210> SEQ ID NO 31
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (2)..(3)
<223> OTHER INFORMATION: the amino acids in these positions can be any
      amino acid
<220> FEATURE:
<221> NAME/KEY: misc_feature
<222> LOCATION: (4)..(4)
<223> OTHER INFORMATION: the amino acid in this position can be either
      Leu or Ile

<400> SEQUENCE: 31

Tyr Xaa Xaa Xaa

<210> SEQ ID NO 32
<211> LENGTH: 16
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (2)..(3)
<223> OTHER INFORMATION: the amino acids in these positions can be any
      amino acid
<220> FEATURE:
<221> NAME/KEY: misc_feature
<222> LOCATION: (4)..(4)
<223> OTHER INFORMATION: the amino acid in this position can be either
      Leu or Ile
<220> FEATURE:
<221> NAME/KEY: misc_feature
<222> LOCATION: (5)..(10)
<223> OTHER INFORMATION: the amino acids in these positions can be any
      amino acid
<220> FEATURE:
<221> NAME/KEY: misc_feature
<222> LOCATION: (11)..(12)
<223> OTHER INFORMATION: The amino acids in these positions may be
      present or absent such that either one or two amino acids are
      present. The amino acids in these positions can be any amino acid
<220> FEATURE:
<221> NAME/KEY: misc_feature
<222> LOCATION: (14)..(15)
<223> OTHER INFORMATION: the amino acids in these positions can be any
      naturally occurring amino acid
<220> FEATURE:
<221> NAME/KEY: misc_feature
<222> LOCATION: (16)..(16)
<223> OTHER INFORMATION: the amino acid in this position can be either
      Leu or Ile

<400> SEQUENCE: 32

Tyr Xaa Xaa Xaa Xaa Xaa Xaa Xaa Xaa Xaa Xaa Xaa Tyr Xaa Xaa Xaa
1               5                   10                  15

<210> SEQ ID NO 33
<211> LENGTH: 9
<212> TYPE: PRT
<213> ORGANISM: Homo sapiens

<400> SEQUENCE: 33

Gln Ser Phe Gly Leu Leu Asp Pro Lys
1               5

<210> SEQ ID NO 34
<211> LENGTH: 27
<212> TYPE: DNA
<213> ORGANISM: Homo sapiens

<400> SEQUENCE: 34
cagagctttg gcctgctgga tcccaaa                                        27

<210> SEQ ID NO 35
<211> LENGTH: 35
<212> TYPE: PRT
<213> ORGANISM: Homo sapiens

<400> SEQUENCE: 35

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp

```
                    20                  25                  30
Val Thr Leu
        35

<210> SEQ ID NO 36
<211> LENGTH: 37
<212> TYPE: PRT
<213> ORGANISM: Homo sapiens

<400> SEQUENCE: 36

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 37
<211> LENGTH: 49
<212> TYPE: PRT
<213> ORGANISM: Homo sapiens

<400> SEQUENCE: 37

His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
            20                  25                  30

Thr Ile Pro Ile Gln Glu Asp Tyr Arg Lys Pro Glu Pro Ala Cys Ser
        35                  40                  45

Pro
```